(12) United States Patent
Rizzardo et al.

(10) Patent No.: US 9,340,498 B2
(45) Date of Patent: May 17, 2016

(54) RAFT POLYMERISATION

(75) Inventors: Ezio Rizzardo, Wheelers Hill (AU);
John Chiefari, Heathmont (AU);
Massimo Benaglia, Bologna (IT); San Thang, Camberwell (AU); Graeme Moad, Sassafras (AU)

(73) Assignee: COMMONWEALTH SCIENTIFIC and INDUSTRIAL RESERACH ORGANISATION, Campbell (AU)

( * ) Notice: Subject to any disclaimer, the term of this patent is extended or adjusted under 35 U.S.C. 154(b) by 1240 days.

(21) Appl. No.: 13/145,993

(22) PCT Filed: Jan. 22, 2010

(86) PCT No.: PCT/AU2010/000065
§ 371 (c)(1),
(2), (4) Date: Sep. 19, 2011

(87) PCT Pub. No.: WO2010/083569
PCT Pub. Date: Jul. 29, 2010

(65) Prior Publication Data
US 2012/0004381 A1 Jan. 5, 2012

(30) Foreign Application Priority Data

Jan. 23, 2009 (AU) .................. 2009900271

(51) Int. Cl.
*C08F 2/38* (2006.01)
*C07C 329/20* (2006.01)
(Continued)

(52) U.S. Cl.
CPC ............. *C07C 329/20* (2013.01); *C07C 333/24* (2013.01); *C07D 213/68* (2013.01); *C07D213/74* (2013.01); *C08F 2/38* (2013.01); *C08F 4/00* (2013.01); *C08F 293/005* (2013.01); *C07D 213/06* (2013.01); *C07D 213/24* (2013.01); *C07D 213/60* (2013.01); *C08F 2438/03* (2013.01)

(58) Field of Classification Search
CPC ..... C08F 2/38; C08F 2438/03; C07D 213/06; C07D 213/24; C07D 213/60
See application file for complete search history.

(56) References Cited

U.S. PATENT DOCUMENTS 6,756,457 B2 6/2004 Wang
2003/0120101 A1 6/2003 Lai
(Continued)

FOREIGN PATENT DOCUMENTS

JP 61207376 A * 9/1986 .......... C07D 213/75
JP 2006-503971 A 2/2006
(Continued)

OTHER PUBLICATIONS

Supplementary European Search Report (SESR) in relation to corresponding European Patent Application No 10733151.4.
(Continued)

*Primary Examiner* — Richard A Huhn
(74) *Attorney, Agent, or Firm* — Arent Fox LLP

(57) ABSTRACT

A method of preparing polymer, the method comprising polymerizing one or more ethylenically unsaturated monomers of formula (I)

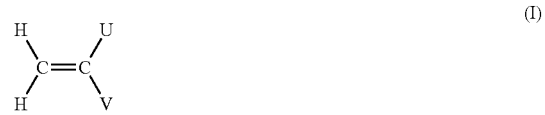

where U is selected from H, $C_1$-$C_4$ alkyl or halogen; V is halogen or of the form O-G where G is selected from —C(O)$R^1$ and —$R^1$, or V is of the form NGG$^a$ where G is as defined above and G$^a$ is selected from H and $R^1$, G and G$^a$ form together with N a heterocyclic ring, or V is of the form $CH_2G^b$ where $G^b$ is selected from H, $R^1$, OH, $OR^1$, $NR^1_2$, $PR^1_2$, $P(O)R^1_2$, $P(OR^1)_2$, $SR^1$, $SOR^1$, and $SO_2R^1$; and where the or each $R^1$ is independently selected from optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted arylalkyl, optionally substituted heteroarylalkyl, optionally substituted alkylaryl, optionally substituted alkylheteroaryl, and an optionally substituted polymer chain, under the control of a RAFT agent of formula (II) or (III),

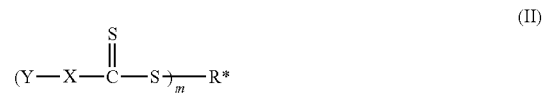

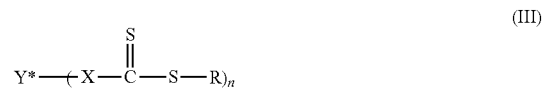

where Y is a Lewis base moiety and Y* is an n-valent Lewis base moiety; X is O or $NR^1$, $R^1$ is as defined above or forms together with Y or Y* and N a heterocyclic ring; m is an integer ≥1; n is an integer ≥2; and where R* is a m-valent radical leaving group that affords R*. which initiates free radical polymerization of the one or more ethylenically unsaturated monomers of formula (I), and R is a free radical leaving group that affords R. which initiates free radical polymerization of the one or more ethylenically unsaturated monomers of formula (I).

4 Claims, No Drawings

(51) Int. Cl.
*C07C 333/24* (2006.01)
*C07D 213/68* (2006.01)
*C07D 213/74* (2006.01)
*C08F 4/00* (2006.01)
*C08F 293/00* (2006.01)
*C07D 213/24* (2006.01)
*C07D 213/06* (2006.01)
*C07D 213/60* (2006.01)

(56) References Cited

U.S. PATENT DOCUMENTS

| | | |
|---|---|---|
| 2003/0232938 A1 | 12/2003 | Charmot et al. |
| 2004/0073056 A1 | 4/2004 | Lai |
| 2004/0110964 A1 | 6/2004 | Achten et al. |
| 2005/0054794 A1 | 3/2005 | Destarac et al. |

FOREIGN PATENT DOCUMENTS

| | | | | |
|---|---|---|---|---|
| JP | 2006-259680 A | 9/2006 | | |
| WO | WO 9928305 A1 * | 6/1999 | ........... | C07D 249/12 |
| WO | WO 2004/037780 A1 | 5/2004 | | |
| WO | WO 2006/122344 A1 | 11/2006 | | |

OTHER PUBLICATIONS

Benaglia et al., "Polystyrene-block-poly(vinyl acetate) through the Use of a Switchable RAFT Agent", *Macromolecules*, American Chemical Society, Washington, DC; US, vol. 42, No. 24, Dec. 22, 2009, pp. 9384-9386.

Destarac et al., "Dithiocarbamates as universal reversible addition-fragmentation chain transfer agents", *Macromolecular Rapid Communications*, Wiley VCH Verlag, Weinheim, DE, vol. 21, No. 15, Oct. 1, 2000, pp. 1035-1039.

Benaglia et al., "Universal (Switchable) RAFT Agents", *Journal of the American Chemical Society*, vol. 131, No. 20, May 27, 2009, pp. 6914-6915.

Quinn et al., "The application of ionizing radiation in reversible addition-fragmentation chain transfer (RAFT) polymerization: Renaissance of a key synthetic and kinetic tool", *Polymer*, Elsevier Science Publishers B.V., GB, vol. 48, No. 22, Oct. 12, 2007, pp. 6467-6480.

Kanagasabapathy et al., "Reversble Addition-Fragmentation Chain-Transfer Polymerization for the Synthesis of Poly(4-acetoxystyrene) and Poly(4-acetoxystyrene)-block-polystyrene by Bulk, Solution and Emulsion Techniques", *Macromol. Rapid Commun.* 2001, 22, 1076-1080.

Cyrille Boyer et al., "Stability and utility of Pyridyl Disulfide Functionality in RAFT and Conventional Radical Polymenzations", *Journal of Polymer Science Part A: Polymer Chemistry*, vol. 46, No. 21, Nov. 1, 2008, pp. 7207-7224.

* cited by examiner

RAFT POLYMERISATION

CROSS-REFERENCE TO RELATED APPLICATION

This application is a National Stage entry of International Application No. PCT/AU2010/000065, filed Jan. 22, 2010, which claims priority to Australian Application No. 2009900271 filed Jan. 23, 2009, the disclosure of the prior applications are incorporated in their entirety by reference.

FIELD OF THE INVENTION

The present invention relates generally to RAFT polymerisation. More specifically, the invention relates to a method for preparing polymer by RAFT polymerisation, to polymers prepared by the method, to block copolymers, and to RAFT agents and precursors thereto.

BACKGROUND OF THE INVENTION

Reversible addition-fragmentation chain transfer (RAFT) polymerisation, as described in International Patent Publication No. WO 98/01478, is a polymerisation technique that exhibits the characteristics associated with living polymerisation. Living polymerisation is generally considered in the art to be a form of chain polymerisation in which irreversible chain termination is substantially absent. An important feature of living polymerisation is that polymer chains will continue to grow while monomer and the reaction conditions to support polymerisation are provided. Polymers prepared by RAFT polymerisation can advantageously exhibit a well defined molecular architecture, a predetermined molecular weight and a narrow molecular weight distribution or low polydispersity.

RAFT polymerisation is believed to proceed under the control of a RAFT agent according to a mechanism which is simplistically illustrated below in Scheme 1.

Scheme 1: Proposed mechanism for RAFT polymerisation, where M represents monomer, $P_n$ represents polymerised monomer, and Z and R are as defined below.

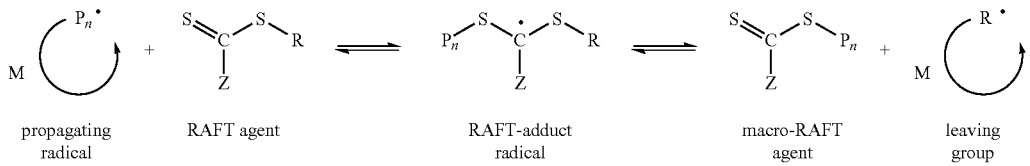

With reference to Scheme 1, R represents a group that functions as a free radical leaving group under the polymerisation conditions employed and yet, as a free radical leaving group, retains the ability to reinitiate polymerisation. Z represents a group that functions to convey a suitable reactivity to the C=S moiety in the RAFT agent towards free radical addition without slowing the rate of fragmentation of the RAFT-adduct radical to the extent that polymerisation is unduly retarded. The ability for both R and Z to function in this way for a given agent is known to be influenced by the nature of the monomer to be polymerised and the polymerisation conditions.

In practice, the R and Z groups of a RAFT agent for use in a given polymerisation reaction are typically selected having regard to the type of monomers that are to be polymerised. For example, it is known in the art that Z groups that afford dithiocarbamate and xanthate RAFT agents can in general be used for controlling the polymerisation of monomers that produce relatively unstabilised propagating radicals (i.e. less activated monomers such as vinyl acetate, N-vinylpyrrolidone and N-vinylcarbazole), whereas Z groups that form dithioester and trithiocarbonate RAFT agents can in general be used for controlling the polymerisation of monomers that produce relatively stabilised propagating radicals (i.e. more activated monomers such as methacrylate esters and styrene). In other words, a given RAFT agent will generally be unsuitable for use in controlling the polymerisation of both less activated and more activated monomers (i.e. monomers having markedly disparate reactivities e.g. styrene and vinyl acetate).

Having said this, under limited circumstances a RAFT agent may be used to polymerise a mixture of less activated and more activated monomers. In that case, those skilled in the art will appreciate that provided the reactivity and mole ratios of the selected monomers are suitable, a RAFT agent may be used to prepare a statistical (or random) copolymer comprising the polymerised residues of less activated and more activated monomers. Those skilled in the art will also appreciate that one practical upshot of this is that to date it has proven difficult to prepare by RAFT polymerisation block copolymers derived from less activated and more activated monomers (e.g. a vinyl acetate-acrylate block copolymer).

It should also be noted that WO 2006/122344 discloses RAFT agents in which Z=F. RAFT agents of this type are said to have the potential to polymerise monomers having disparate reactivities. However, such RAFT agents are generally difficult to synthesise, they may be unstable under certain polymerisation conditions, and their effectiveness has yet to be proven.

Although there are numerous advantages to be gained by employing conventional methods for polymerising monomers under the control of a RAFT agent to form polymer, it would be nonetheless desirable to provide a RAFT polymerisation method and RAFT agents that offered further utility relative to those currently known.

SUMMARY OF THE INVENTION

The present invention therefore provides a method of preparing polymer, the method comprising polymerising one or more ethylenically unsaturated monomers of formula (I)

where U is selected from H, $C_1$-$C_4$ alkyl or halogen; V is halogen or of the form O-G where G is selected from —C(O)$R^1$ and —$R^1$, or V is of the form NG$G^a$ where G is as defined above and $G^a$ is selected from H and $R^1$, or G and $G^a$ form together with N a heterocyclic ring, or V is of the form $CH_2G^b$ where $G^b$ is selected from H, $R^1$, OH, $OR^1$, $NR^1{}_2$, $PR^1{}_2$, $P(O)R^1{}_2$, $P(OR^1)_2$, $SR^1$, $SOR^1$, and $SO_2R^1$; and where the or each $R^1$ is independently selected from optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted arylalkyl, optionally substituted heteroarylalkyl, optionally substituted alkylaryl, optionally substituted alkylheteroaryl, and an optionally substituted polymer chain, under the control of a RAFT agent of formula (II) or (III),

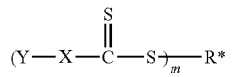
(II)

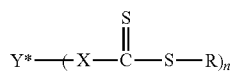
(III)

where Y is a Lewis base moiety and Y* is an n-valent Lewis base moiety; X is O or $NR^1$, $R^1$ is as defined above or forms together with Y or Y* and N a heterocyclic ring; m is an integer ≥1; n is an integer ≥2; and where R* is a m-valent radical leaving group that affords R*. which initiates free radical polymerisation of the one or more ethylenically unsaturated monomers of formula (I), and R is a free radical leaving group that affords R. which initiates free radical polymerisation of the one or more ethylenically unsaturated monomers of formula (I).

In some embodiments of the invention, the Lewis base moiety comprises a Lewis basic nitrogen atom (N) (i.e. a nitrogen atom that is capable of donating an electron pair).

RAFT agents of formula (II) and (III) have a Lewis base moiety covalently bound to X and are suitable for use in the polymerisation of less activated monomers (i.e. those of formula (I)). It has now been found that when the Lewis base moiety is in the form of a Lewis adduct (i.e. where the Lewis base moiety is associated with a Lewis acid moiety) the agents can also be used to control the polymerisation of more activated monomers. Furthermore, the Lewis acid moiety can be reversibly associated with the Lewis base moiety. The RAFT agents of formula (II) and (III) may therefore be provided in the form of macro-RAFT agents which have been prepared by the polymerisation of more activated monomers under the control of Lewis adducts of formula (II) and (III).

Accordingly, in one embodiment of the invention the RAFT agents of formula (II) and (III) are macro-RAFT agents prepared by a method comprising:
(i) polymerising one or more ethylenically unsaturated monomers of formula (IV)

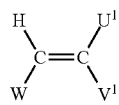
(IV)

where W is H or forms together with $V^1$ a lactone, anhydride or imide ring; $U^1$ is selected from H, $C_1$-$C_4$ alkyl, $CO_2R^1$ and halogen; $V^1$ forms together with W a lactone, anhydride or imide ring, or is selected from optionally substituted aryl, alkenyl, $CO_2H$, $CO_2R^1$, $COR^1$, CN, $CONH_2$, $CONHR^1$, $CONR^1{}_2$, $PO(OR^1)_2$, $PO(R^1)_2$, $PO(OH)R^1$, $PO(OH)_2$, $SO(OR^1)$, $SO_2(OR^1)$, $SOR^1$ and $SO_2R^1$; and where the or each $R^1$ is as defined above, under the control of a RAFT agent Lewis adduct of formula (V) or (VI), respectively,

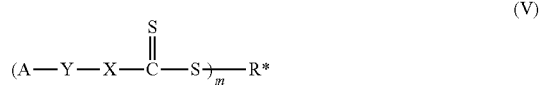
(V)

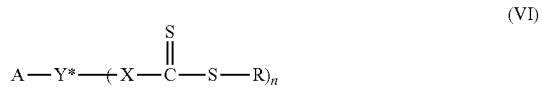
(VI)

where Y, X, m and n are as defined above; Y* is an (n+1)-valent Lewis base moiety; A is a Lewis acid moiety associated with Y or Y* forming the respective adducts; R* is a m-valent radical leaving group that affords R*. which initiates free radical polymerisation of the one or more ethylenically unsaturated monomers of formula (IV), and where R is a free radical leaving group that affords R. which initiates free radical polymerisation of the one or more ethylenically unsaturated monomers of formula (IV), to form a macro-RAFT agent Lewis adduct; and
(ii) disassociating A from Y or Y* in the so formed macro-RAFT agent Lewis adduct to thereby form the macro-RAFT agents.

By this method, a RAFT agent Lewis adduct of formula (V) or (VI) may be used in a first RAFT polymerisation to form a macro-RAFT agent Lewis adduct comprising a block of more activated monomers (i.e. monomers of formula (IV)). Using the so formed macro-RAFT agent Lewis adduct, A can then be disassociated from Y or Y* to form a macro-RAFT agent, which in turn can be used in a second RAFT polymerisation to form a subsequent block of less activated monomers (i.e. monomers of formula (I)).

Accordingly, in the form of a multi-stage RAFT polymerisation process, the present invention also provides a method of preparing polymer, the method comprising:
(i) polymerising one or more ethylenically unsaturated monomers of formula (IV)

(IV)

where W is H or forms together with $V^1$ a lactone, anhydride or imide ring; $U^1$ is selected from H, $C_1$-$C_4$ alkyl, $CO_2R^1$ and halogen; $V^1$ forms together with W a lactone, anhydride or imide ring or is selected from optionally substituted aryl, alkenyl, $CO_2H$, $CO_2R^1$, $COR^1$, CN, $CONH_2$, $CONHR^1$, $CONR^1{}_2$, $PO(OR^1)_2$, $PO(R^1)_2$, $PO(OH)R^1$, $PO(OH)_2$, $SO(OR^1)$, $SO_2(OR^1)$, $SOR^1$ and $SO_2R^1$; and where the or each $R^1$ is independently selected from optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted arylalkyl, optionally substituted heteroarylalkyl, optionally substituted alkylaryl, optionally substituted alkylheteroaryl, and an optionally substituted polymer chain, under the control of a RAFT agent Lewis adduct of formula (V) or (VI),

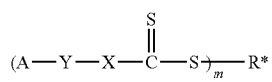

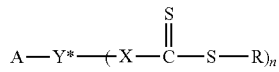

where Y is a Lewis base moiety and Y* is an (n+1)-valent Lewis base moiety; X is O or $NR^1$, $R^1$ is as defined above or forms together with Y and N a heterocyclic ring; m is an integer $\geq 1$; n is an integer $\geq 2$; A is a Lewis acid moiety associated with Y or Y* forming the respective adducts; R* is a m-valent radical leaving group that affords R*. which initiates free radical polymerisation of the one or more ethylenically unsaturated monomers of formula (IV); and where R is a free radical leaving group that affords R. which initiates free radical polymerisation of the one or more ethylenically unsaturated monomers of formula (IV), to form a macro-RAFT agent Lewis adduct;
(ii) disassociating A from Y or Y* in the so formed macro-RAFT agent Lewis adduct to thereby form a macro-RAFT agent; and
(iii) polymerising one or more ethylenically unsaturated monomers of formula (I)

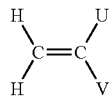

where U is selected from H, $C_1$-$C_4$ alkyl or halogen; V is halogen or of the form O-G where G is selected from —C(O)$R^1$ and —$R^1$, or V is of the form $NGG^a$ where G is as defined above and $G^a$ is selected from H and $R^1$, or G and $G^a$ form together with N a heterocyclic ring, or V is of the form $CH_2G^b$ where $G^b$ is selected from H, $R^1$, OH, $OR^1$, $NR^1_2$, $PR^1_2$, P(O)$R^1_2$, P(O$R^1$)$_2$, $SR^1$, $SOR^1$, and $SO_2R^1$; and where the or each $R^1$ is independently selected from optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted arylalkyl, optionally substituted heteroarylalkyl, optionally substituted alkylaryl, optionally substituted alkylheteroaryl, and an optionally substituted polymer chain, under the control of the macro-RAFT formed in step (ii).

RAFT agents of formula (V) or (VI) may of course be used only in controlling the polymerisation of monomers of formula (IV).

In a further aspect, the present invention therefore also provides a method of preparing polymer, the method comprising polymerising one or more ethylenically unsaturated monomers of formula (IV)

where W is H or forms together with $V^1$ a lactone, anhydride or imide ring; $U^1$ is selected from H, $C_1$-$C_4$ alkyl, $CO_2R^1$ and halogen; $V^1$ forms together with W a lactone, anhydride or imide ring, or is selected from optionally substituted aryl, alkenyl, $CO_2H$, $CO_2R^1$, $COR^1$, CN, $CONH_2$, $CONHR^1$, $CONR^1_2$, PO($OR^1$)$_2$, PO($R^1$)$_2$, PO(OH)$R^1$, PO(OH)$_2$, SO($OR^1$), $SO_2$($OR^1$), $SOR^1$ and $SO_2R^1$; and where the or each $R^1$ is independently selected from optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted arylalkyl, optionally substituted heteroarylalkyl, optionally substituted alkylaryl, optionally substituted alkylheteroaryl, and an optionally substituted polymer chain, under the control of a RAFT agent Lewis adduct of formula (V) or (VI),

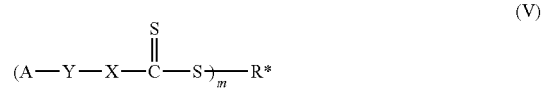

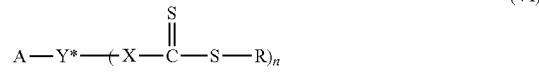

where Y is a Lewis base moiety; Y* is an (n+1)-valent Lewis base moiety; X is O or $NR^1$, $R^1$ forms together with Y and N a heterocyclic ring, or $R^1$ is independently selected from optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted arylalkyl, optionally substituted heteroarylalkyl, optionally substituted alkylaryl, optionally substituted alkylheteroaryl, and an optionally substituted polymer chain; m is an integer $\geq 1$; n is an integer $\geq 2$; A is a Lewis acid moiety associated with Y or Y* forming the respective adducts; R* is a m-valent radical leaving group that affords R*. which initiates free radical polymerisation of the one or more ethylenically unsaturated monomers of formula (IV), and where R is a free radical leaving group that affords R. which initiates free radical polymerisation of the one or more ethylenically unsaturated monomers of formula (IV).

In accordance with the methods of the invention, two or more different monomers of formula (I) or two or more different monomers of formula (IV) may be polymerised as a mixture or sequentially under the control of the RAFT agents. In other words, two or more different monomers of formula (I) may be polymerised sequentially such that the polymer chain segment formed in this step is a block or multi-block copolymer, or these monomers may be polymerised together as a monomer mixture such that the polymer chain formed is a statistical copolymer, or these monomers may be polymerised as a combination of such possibilities. Similarly, two or more different monomers of formula (IV) may be polymerised sequentially such that the polymer chain segment formed in this step is a block or multi-block copolymer, or these monomers may be polymerised together as a monomer mixture such that the polymer chain formed is a statistical copolymer, or these monomers may be polymerised as a combination of such possibilities A monomer mixture formed from one or more monomers of formula (I) and one or more monomers of formula (IV) may also be polymerised under the control of the RAFT agents. In other words, a monomer mixture formed from one or more monomers of formula (I) and one or more monomers of formula (IV) may be polymerized such that the polymer chain formed is a statistical copolymer. This mode of monomer polymerisation may of course be conducted in combination with those outlined directly above.

Those skilled in the art will appreciate that the sequential RAFT polymerisation steps (i) and (iii) in the method above can afford novel copolymers derived from the polymerised residues of monomers of formulae (IV) and (I). This mode of polymerisation is particularly suited to preparing block copolymers.

The present invention further provides polymers prepared in accordance with the methods of the invention, and also novel RAFT agents and precursors thereto as defined below suitable for use in accordance with the methods of the invention.

The present invention also provides a polymer comprising a moiety of formula (VII) or (VIII)

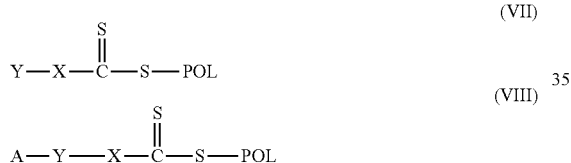

where Y is a Lewis base moiety; X is O or $NR^1$, $R^1$ forms together with Y and N a heterocyclic ring, or $R^1$ is independently selected from optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted arylalkyl, optionally substituted heteroarylalkyl, optionally substituted alkylaryl, optionally substituted alkylheteroaryl, and an optionally substituted polymer chain; A is a Lewis acid moiety associated with Y forming a Lewis adduct; POL is a polymerised residue of one or more ethylenically unsaturated monomers.

The present invention also provides a polymer comprising a moiety of formula (VIIa) or (VIIIa)

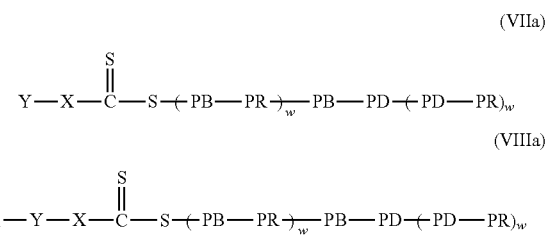

where Y is a Lewis base moiety; X is O or $NR^1$, $R^1$ forms together with Y and N a heterocyclic ring, or $R^1$ is independently selected from optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted arylalkyl, optionally substituted heteroarylalkyl, optionally substituted alkylaryl, optionally substituted alkylheteroaryl, and an optionally substituted polymer chain; A is a Lewis acid moiety associated with Y forming a Lewis adduct; PB is a polymerised residue of one or more ethylenically unsaturated monomers of formula (I); PD is a polymerised residue of one or more ethylenically unsaturated monomers of formula (IV); PR is a polymerised residue of a monomer mixture formed from one or more ethylenically unsaturated monomers of formula (I) and one or more ethylenically unsaturated monomers of formula (IV); and where each w is independently 0 or 1;

where U is selected from H, $C_1$-$C_4$ alkyl or halogen; V is halogen or of the form O-G where G is selected from —$C(O)R^1$ and —$R^1$, or V is of the form $NGG^a$ where G is as defined above and $G^a$ is selected from H and $R^1$, or G and $G^a$ form together with N a heterocyclic ring, or V is of the form $CH_2G^b$ where $G^b$ is selected from H, $R^1$, OH, $OR^1$, $NR^1_2$, $PR^1_2$, $P(O)R^1_2$, $P(OR^1)_2$, $SR^1$, $SOR^1$, and $SO_2R^1$; and where the or each $R^1$ is as defined above;

where W is H or forms together with $V^1$ a lactone, anhydride or imide ring; $U^1$ is selected from H, $C_1$-$C_4$ alkyl, $CO_2R^1$ and halogen; $V^1$ forms together with W a lactone, anhydride or imide ring or is selected from optionally substituted aryl, alkenyl, $CO_2H$, $CO_2R^1$, $COR^1$, CN, $CONH_2$, $CONHR^1$, $CONR^1_2$, $PO(OR^1)_2$, $PO(R^1)_2$, $PO(OH)R^1$, $PO(OH)_2$, $SO(OR^1)$, $SO_2(OR^1)$, $SOR^1$ and $SO_2R^1$; and where the or each $R^1$ is as defined above.

The moieties (VII), (VIII), (VIIa) and (VIIIa) above comprise structural elements of a polymer that may be prepared according to the present invention. The moieties may of course form part of more complex polymer structures. For example, the moieties may represent a branch arm of a star polymer. The polymer chain of the moieties may also terminate with a R or R* group as hereinbefore defined, the likes of which is derived from the RAFT agent used to prepare the moieties.

Those skilled in the art will appreciate that the methods of the present invention expand the utility of xanthate and dithiocarbamate RAFT agents by employing a Lewis base moiety covalently bound to their respective O and N atoms (represented as X in the formulae above). Without wishing to be limited by theory, it is believed that formation of a Lewis adduct between the Lewis base moeity and a Lewis acid moiety promotes a change in the reactivity of the C=S moiety of the agent toward free radical addition relative to when the agent is in its "free base" form. The ability to change or switch the agent's reactivity toward free radical addition advantageously enables a given agent to be used in the polymerisation of monomers having markedly disparate reactivities. Such agents can therefore not only be used to polymerise more activated or less activated monomers, but they can also be used to prepare block copolymers from such monomers that have to date been difficult to prepare using conventional RAFT polymerisation methods/agents.

These and other aspects of the invention are described in more detail below.

DETAILED DESCRIPTION OF THE INVENTION

In accordance with the methods of the invention, one or more ethylenically unsaturated monomers are polymerised under the control of a specified RAFT agent. By being polymerised "under the control" of the RAFT agent is meant that polymerisation of the monomer proceeds via a reversible addition-fragmentation chain transfer (RAFT) mechanism to form polymer.

Polymers prepared by RAFT polymerisation can advantageously exhibit a well defined molecular architecture, a predetermined molecular weight and a narrow molecular weight distribution or low polydispersity. Polymers prepared by RAFT polymerisation will typically have a lower polydispersity compared with the polymerisation being conducted in the absence of the RAFT agent. By being polymerised under the control of a RAFT agent, the resulting polymer can have a polydispersity of less than about 2.0, for example of less than about 1.5, or less than about 1.2. Such polydispersity values may be attainable at a percent monomer conversion of at least 30%, for example of at least 40%, or at least 50%, or at least 60%, or at least 70%.

By the ethylenically unsaturated monomers being "polymerised" under the control of the RAFT agent is meant that at least a single monomer residue is inserted adjacent the —S— atom of the agent according to the RAFT mechanism. Generally two or more monomer residues will be inserted adjacent the —S— atom of the agent according to the RAFT mechanism.

By one or more "ethylenically unsaturated monomers" is meant one or more one or more ethylenically unsaturated monomers of formula (I) and/or one or more ethylenically unsaturated monomers of formula (IV).

The monomers used in accordance with the invention have the general formula (I) or (IV)

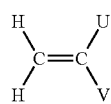
(I)

where U is selected from H, $C_1$-$C_4$ alkyl or halogen; V is halogen or of the form O-G where G is selected from —C(O)$R^1$ and —$R^1$, or V is of the form NGG$^a$ where G is as defined above and G$^a$ is selected from H and $R^1$, G and G$^a$ form together with N a heterocyclic ring, or V is of the form $CH_2G^b$ where G$^b$ is selected from H, $R^1$, OH, O$R^1$, N$R^1_2$, P$R^1_2$, P(O)$R^1_2$, P(O$R^1$)$_2$, S$R^1$, SO$R^1$, and SO$_2R^1$; and where the or each $R^1$ is independently selected from optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted arylalkyl, optionally substituted heteroarylalkyl, optionally substituted alkylaryl, optionally substituted alkylheteroaryl, and an optionally substituted polymer chain,

(IV)

where W is H or forms together with $V^1$ a lactone, anhydride or imide ring; $U^1$ is selected from H, $C_1$-$C_4$ alkyl, $CO_2R^1$ and halogen; $V^1$ forms together with W a lactone, anhydride or imide ring or is selected from optionally substituted aryl, alkenyl, $CO_2H$, $CO_2R^1$, $COR^1$, CN, $CONH_2$, $CONHR^1$, $CONR^1_2$, $PO(OR^1)_2$, $PO(R^1)_2$, $PO(OH)R^1$, $PO(OH)_2$, $SO(OR^1)$, $SO_2(OR^1)$, $SOR^1$ and $SO_2R^1$; and where the or each $R^1$ is independently selected from optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted arylalkyl, optionally substituted heteroarylalkyl, optionally substituted alkylaryl, optionally substituted alkylheteroaryl, and an optionally substituted polymer chain.

The or each $R^1$ may also be independently selected from optionally substituted $C_1$-$C_{22}$ alkyl, optionally substituted $C_2$-$C_{22}$ alkenyl, optionally substituted $C_2$-$C_{22}$ alkynyl, optionally substituted $C_6$-$C_{18}$ aryl, optionally substituted $C_3$-$C_{18}$ heteroaryl, optionally substituted $C_3$-$C_{18}$ carbocyclyl, optionally substituted $C_2$-$C_{18}$ heterocyclyl, optionally substituted $C_7$-$C_{24}$ arylalkyl, optionally substituted $C_4$-$C_{18}$ heteroarylalkyl, optionally substituted $C_7$-$C_{24}$ alkylaryl, optionally substituted $C_4$-$C_{18}$ alkylheteroaryl, and an optionally substituted polymer chain.

The or each $R^1$ may also be independently selected from optionally substituted $C_1$-$C_{22}$ alkyl, optionally substituted $C_2$-$C_{22}$ alkenyl, $C_2$-$C_{22}$ optionally substituted alkynyl, optionally substituted aryl, optionally substituted heteroaryl, optionally substituted carbocyclyl, optionally substituted heterocyclyl, optionally substituted arylalkyl, optionally substituted heteroarylalkyl, optionally substituted alkylaryl, optionally substituted alkylheteroaryl, and an optionally substituted polymer chain.

In one embodiment, $R^1$ may be independently selected from optionally substituted $C_1$-$C_4$ alkyl.

Examples of optional substituents for $R^1$ include those selected from alkyleneoxidyl (epoxy), hydroxy, alkoxy, acyl, acyloxy, formyl, alkylcarbonyl, carboxy, sulfonic acid, alkoxy- or aryloxy-carbonyl, isocyanato, cyano, silyl, halo, amino, including salts and derivatives thereof. Examples polymer chains include those selected from polyalkylene oxide, polyarylene ether and polyalkylene ether.

In the context of RAFT polymerisation, those skilled in the art will appreciate that monomers of formula (I) and (IV) are considered to have disparate reactivates. In particular, monomers of formula (I) are generally considered to be less activated toward RAFT polymerisation in that during polymerisation the carbon atom bearing the unpaired electron is attached to a sp$^3$ hybridised carbon, oxygen, nitrogen, or halogen atom and therefore provides for a relatively unstabilised propagating radical. Monomers of formula (IV) are generally considered to be more activated toward RAFT polymerisation in that during polymerisation the carbon atom bearing the unpaired electron is attached to a sp or $sp^2$ hybridised carbon atom that forms part of a double or triple bond, or are attached to a phosphorous or sulphur atom, and therefore provides for a relatively stabilised propagating radical.

Reference herein to the ethylenically unsaturated monomers used in accordance with the invention having "disparate reactivities" is intended to relate to the relative reactivities of the monomers in the context of RAFT polymerisation.

Examples of "less activated" monomers (i.e. monomers of formula (I)) include vinylethers, vinyl alkanoates, vinyl halides, N-vinyl amides, N-vinyl lactams, N-vinyl heteroarmoatics, vinyl silanes, vinyl phosphates and allyl or diallyl monomers.

Specific examples of "less activated" monomers (i.e. monomers of formula (I)) include vinyl acetate, vinyl propionate; vinyl butyrate, vinyl decanoate, vinyl neodecanoate, vinyl stearate; vinyl trifluoroacetate; vinyl benzoate, vinylester-based glycomonomers, ethyl vinyl ether, vinyl chloride, vinyl fluoride, vinyl bromide, N-vinylformamide, N-vinyl-N-methylacetamide, N-vinylphthalimide, N-vinylpyrrolidone, N-vinylcaprolactam, N-vinylcarbazole, vinyl trimethylsilane, vinyltriphenylsilane, vinyltrimethoxysilane, vinyltriethoxysilane, and diallyldimethylammonium chloride.

Examples of "more activated" monomers (i.e. monomers of formula (IV)) include acrylates, methacrylates, styenics, vinyl aromatics and heteroaromatics, conjugated dienes, acrylamides, methacrylamides, acrylonitrile, methacrylonitrile, maleic anhydride and maleimides, vinyl sulphones, vinyl sulphoxides, vinyl phosphinates, vinyl phosphonates, and combinations thereof.

Specific examples of "more activated" monomers (i.e. monomers of formula (IV)) include methyl methacrylate, ethyl methacrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, functional methacrylates, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolmethacrylamide, N-ethylolmethacrylamide, N-tert-butylacrylamide, N-n-butylacrylamide, N-methylolacrylamide, N-ethylolacrylamide, vinyl benzoic acid (all isomers), diethylamino styrene (all isomers), alpha-methylvinyl benzoic acid (all isomers), diethylamino alpha-methylstyrene (all isomers), p-vinylbenzene sulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysilylpropyl methacrylate, trimethoxysilylpropyl acrylate, triethoxysilylpropyl acrylate, tributoxysilylpropylacrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, maleic anhydride, N-phenylmaleimide, N-butylmaleimide, butadiene, chloroprene, acenapthalene, vinylnapthalene, vinylbiphenyl, vinyl azlactone; 1-vinylimidazole; 2-vinylpyridine, 4-vinyl pyridine, α-methylene-γ-butyrolactone, 2-methacryloxyethyl glucoside (any anomer), and vinylferrocene.

Where monomers of formula (I) are polymerised in accordance with the invention, the monomers used may be the same so as to provide for a homopolymer, or two or more different such monomers may be used so as to provide for a copolymer.

Where monomers of formula (IV) are polymerised in accordance with the invention, the monomers used may be the same so as to provide for a homopolymer or two or more different such monomers may be used so as to provide for a copolymer.

A mixture of monomers of formula (I) and (IV) may also be polymerised in accordance with the invention.

Factors that determine the copolymerisability of various monomers are well documented in the art. For example, see: Greenlee, R. Z., in Polymer Handbook $3^{rd}$ Edition (Brandup, J., and Immergut. E. H. Eds) Wiley: New York, 1989 p II/53.

Monomers suitable for RAFT polymerization may be formed by converting compounds with hydroxyl functionality to (meth)acrylates or vinylbenzyl ethers. Similarly compounds with amino functionality can be converted to methacrylamides and compounds with aldehyde functionality can be converted to vinyl esters. Examples of this include the conversion of sugars such as glucose to (meth)acrylate- and (meth)acrylamide-based glycomonomers and the conversion of aminoacids or ω-amino-oligopeptides to the corresponding (meth)acrylamide derivative.

A further summary of monomers amenable to RAFT polymerization can be found in recent reviews such as Moad et al, Polymer 49 (2008), 1079-1131.

In one aspect of the invention, one or more ethylenically unsaturated monomers of formula (I) are polymerised under the control of a RAFT agent of formula (II) or (III)

(II)

(III)

where Y is a Lewis base moiety; Y* is an n-valent Lewis base moiety; X is O or $NR^1$, $R^1$ is as defined above or forms together with Y or Y* and N a heterocyclic ring; m is an integer ≥1; n is an integer ≥2; R* is a m-valent radical leaving group that affords R*. which initiates free radical polymerisation of the one or more ethylenically unsaturated monomers of formula (I); and where R is a free radical leaving group that affords R. which initiates free radical polymerisation of the one or more ethylenically unsaturated monomers of formula (I).

In a further aspect of the invention, one or more ethylenically unsaturated monomers of formula (IV) are polymerised under the control of a RAFT agent of formula (V) or (VI),

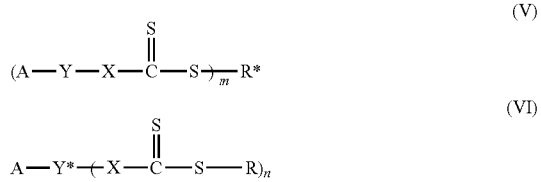

where Y is a Lewis base moiety; Y* is an (n+1)-valent Lewis base moiety; X is O or $NR^1$, $R^1$ is as defined above or forms together with Y or Y* and N a heterocyclic ring; m and n are as defined above; A is a Lewis acid moiety associated with Y or Y* forming the respective adducts; R* is a m-valent radical leaving group that affords R*. which initiates free radical polymerisation of the one or more ethylenically unsaturated monomers of formula (IV), and where R is a free radical leaving group that affords R. which initiates free radical polymerisation of the one or more ethylenically unsaturated monomers of formula (IV).

Those skilled in the art will appreciate that RAFT agents used in accordance with the invention are xanthate and dithiocarbamate RAFT agents. These RAFT agents comprise a Lewis base moiety Y or Y* covalently attached to an O or N atom. By "Lewis base moiety" is meant a moiety that can function as an electron-pair donor. As will be discussed in more detail below, the Lewis base moiety will be capable of reversibly associating with a Lewis acid moiety to form a Lewis adduct. By "Lewis acid moiety" is meant a moiety capable of accepting an electron pair. By "Lewis adduct" is meant the product formed through a Lewis base moiety donating an electron pair to a Lewis acid moiety so as to form a bond therebetween (i.e. the Lewis acid moiety is associated with the Lewis base moiety).

Those skilled in the art will appreciate that upon adduct formation, A in formula (V) and (VI) may not retain Lewis acidic properties per se, and Y and Y* in formula (V) and (VI) may not retain Lewis basic properties per se. In other words, the association of A with Y or Y* to form an adduct can in effect "neutralise" their respective Lewis acidic and Lewis basic properties. Nevertheless, for convenience A in the RAFT agents of the invention will herein be referred to as a Lewis acid moiety, and Y and Y* in the RAFT agents of the invention will herein be referred to as a Lewis base moiety.

In formula (III), the Lewis base moiety Y* is an n-valent Lewis base moiety, with n being an integer ≥2. Those skilled in the art will appreciate that a Lewis base moiety of this type will be at least di-valent. Y* may therefore be di-valent, tri-valent or of higher valency. For example, Y* may be an optionally substituted polymer chain with the remainder of the RAFT agent depicted in formula (III) presented as multiple groups pendant from the polymer. In that case, n may be an integer as high as 20, 50, 100, 200, 500 or even 1000. In some embodiments, n will be an integer ranging from 2 to 10, for example from 2 to 4.

In formula (V) and (VI), Y and Y* are each a Lewis base moiety as herein defined, but are also associated with a Lewis acid moiety (A) so as to form a Lewis adduct. By virtue of the association with A, Y in formula (V) is of course depicted as a di-valent Lewis base moiety and Y* in formula (VI) is of course depicted as a (n+1)-valent Lewis base moiety. In the context of formula (IV), n is as defined in respect of formula (III)

There is no particular limitation on the type of Lewis base moiety that may be used in accordance with the invention provided it can form a Lewis adduct with a Lewis acid and the so formed Lewis adduct renders the agent suitable for use in controlling the polymerisation of monomers of formula (IV).

Provided that a suitable RAFT agent Lewis adduct can be formed, there is no particular limitation on the type of Lewis acid moiety A that may be used in accordance with the invention. For example, in the form of an adduct the Lewis acid moiety A may be —H. In that case, those skilled in the art will appreciate, and as will be discussed in more detail below, the —H is formed through association of the Lewis base moiety with $H^+$, which itself can be derived from a protic acid.

Other suitable Lewis acid moieties include metal salts such as metal triflates (e.g. aluminium triflate and ytterbium triflate), and metal alkanoates (e.g. stannous octoate).

A "RAFT agent Lewis adduct" in the context of the present invention is therefore intended to mean a xanthate or dithiocarbamate RAFT agent having a Lewis base moiety covalently bound to the xanthate oxygen atom or dithiocarbamate nitrogen atom, with the Lewis base moiety being associated with a Lewis acid moiety so as to form the RAFT agent Lewis adduct. This may be further illustrated with reference to formula (Va), which falls within the scope of formula (V) above, where R* is as defined above, and in terms of formula (V), m=1, X=$NR^1$, Y=pyridyl in adduct formation with A=H.

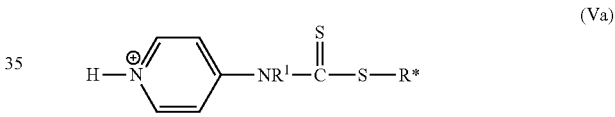

Without wishing to be limited by theory, formation of the Lewis adduct (e.g. formula (V) and (VI)) is believed to cause a change in the reactivity of the C=S moiety toward free radical addition relative to the C=S moiety of the agent in its free base form (e.g. formula (II) and (III)). In particular, the A-Y— and A-Y*— moieties of formula (V) and (VI), respectively, are believed to promote this effect by functioning as electron withdrawing groups that are in conjugation, inductive and/or field (also referred to as "through space") communication with the N or O atom of the X group. This in turn is believed to change the reactivity of the C=S moiety toward free radical addition by rendering the C=S moiety less electron rich relative to the agent in its free base from.

Suitable Lewis bases for use in accordance with the invention are therefore believed to include those that, upon reaction with a Lewis acid, form a Lewis adduct moiety which is in conjugation, inductive and/or field communication with the N or O atom of the X group.

By the Lewis adduct moiety being in "communication" with the N or O atom of the X group is meant that the electron withdrawing effect provided by the Lewis adduct moiety is conveyed through to the N or O atom of the X group, thereby rendering the C=S moiety of the agent less electron rich relative to the agent in its free base from.

The Lewis base moiety will comprise a Lewis basic heteroatom that gives rise to the Lewis basic properties of the moiety and provides an electron pair that is involved in adduct formation. Suitable heteroatoms include N, S, P and Se. The "communication" between the Lewis adduct and the N or O atom of the X group may therefore be also described in terms of a communication between the Lewis basic heteroatom and the N or O atom of the X group.

In one embodiment, the Lewis base moiety comprises a N atom. In a further embodiment, the Lewis base moiety derives its Lewis basic properties only from a N atom.

Where the communication is by inductive effect alone, the Lewis basic heteroatom will generally form part of the Lewis base moiety such that it is no further than 5, preferably no further than 4, more preferably no further than 3 atoms removed from the O or N atom of the X group. A Lewis basic heteroatom that provides an inductive effect may be located more than 3, 4 or 5 atoms removed from the O or N atom of the X group provided that there is conjugation from that heteroatom to one or two atoms removed from the O or N atom of the X group. Those skilled in the art will appreciate that such proximity considerations apply to ensure that the inductive effect remains strong enough to promote a change in the reactivity of the C=S moiety.

The electron withdrawing effect is believed to be most prominent where the Lewis base moiety Y— or Y*— is of a type that is capable of forming a Lewis adduct moiety that is in conjugation communication with the O or N atom of the X group. In other words, the Lewis base moiety is of a type comprising a Lewis basic heteroatom that is in conjugation communication with the O or N atom of the X group. Those skilled in the art will appreciate what is meant by "conjugation", and this may be further explained with reference to Scheme 2 below. This, Scheme 2 illustrates how the electron withdrawing effect of the Lewis adduct moiety of the RAFT agent Lewis adduct (Va) can be conveyed to the X group through resonance structure (Vb).

More specific examples of Lewis base moieties include optionally substituted pyridyl (all isomers, i.e. ortho, meta and para with respect to the N atom that forms part of the ring) and optionally substituted N,N-dialkylaminophenyl (all isomers, i.e. ortho, meta and para with respect to the N atom attached to the ring).

R and R* in the RAFT agents used in accordance with the methods of the invention will be selected so as to function as a free radical leaving group under the polymerisation conditions employed and yet, as a free radical leaving group, retain the ability to reinitiate polymerisation of the selected monomers. Those skilled in the art will be able to readily select a suitable R or R* group for a given polymerisation, for example see Moad et al, Polymer 49 (2008), 1079-1131.

In a similar manner to that described above in respect of Y*, R* is a m-valent radical leaving group, with m being an integer ≥1. R* may therefore be mono-valent, di-valent, tri-valent or of higher valency. For example, R* may be an optionally substituted polymer chain with the remainder of the RAFT agent depicted in formula (II) presented as multiple groups pendant from the polymer. In that case, m may be an integer as high as 20, 50, 100, 200, 500 or even 1000. In some embodiments, m will be an integer ranging from 1 to 10, for example from 1 to 5.

Examples of R in RAFT agents used in accordance with the invention include optionally substituted, and in the case of R* in RAFT agents used in accordance with the invention include a m-valent form of optionally substituted, alkyl, alkenyl, alkynyl, aryl, acyl, carbocyclyl, heterocyclyl, heteroaryl, alkylthio, alkenylthio, alkynylthio, arylthio, acylthio, carbocyclylthio, heterocyclylthio, heteroarylthio, alkylalkenyl, alkylalkynyl, alkylaryl, alkylacyl, alkylcarbocyclyl, Scheme 2: Proposed resonance structures of a macro-RAFT agent Lewis adduct of formula (Va).

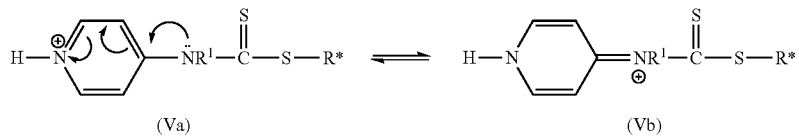

(Va)    (Vb)

Examples of suitable Lewis base moieties therefore include those comprising: a Lewis basic heteroatom that it is no further than 5, preferably no further than 4, more preferably no further than 3 atoms removed from the O or N atom of the X group, a Lewis basic heteroatom that is more than 3, 4 or 5 atoms removed from the O or N atom of the X, wherein the heteroatom is conjugated with an α or β atom (e.g. a carbon atom) relative to the O or N atom of the X group, and/or a Lewis basic heteroatom that is conjugated with the O or N atom of the X group.

Suitable Lewis base moieties are preferably those comprising a Lewis basic heteroatom that is conjugated with the O or N atom of the X group.

Specific examples of Lewis base moieties include optionally substituted heteroaryl and optionally substituted aryl-Q, where Q=NR$^1$R$^1$, SR$^1$, PR$^1$R$^1$, and SeR$^1$, and the or each R$^1$ is independently selected from optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted arylalkyl, optionally substituted heteroarylalkyl, optionally substituted alkylaryl, optionally substituted alkylheteroaryl, and an optionally substituted polymer chain. In some embodiments, Q=NR$^1$R$^1$.

alkylheterocyclyl, alkylheteroaryl, alkyloxyalkyl, alkenyloxyalkyl, alkynyloxyalkyl, aryloxyalkyl, alkylacyloxy, alkylcarbocyclyloxy, alkylheterocyclyloxy, alkylheteroaryloxy, alkylthioalkyl, alkenylthioalkyl, alkynylthioalkyl, arylthioalkyl, alkylacylthio, alkylcarbocyclylthio, alkylheterocyclylthio, alkylheteroarylthio, alkylalkenylalkyl, alkylalkynylalkyl, alkylarylalkyl, alkylacylalkyl, alkylkylaryl, arylalkenylaryl, arylalkynylaryl, arylacylaryl, arylacyl, arylcarbocyclyl, arylheterocyclyl, arylheteroaryl, alkenyloxyaryl, alkynyloxyaryl, aryloxyaryl, alkylthioaryl, alkenylthioaryl, alkynylthioaryl, arylthioaryl, arylacylthio, arylcarbocyclylthio, arylheterocyclylthio, arylheteroarylthio, and an optionally substituted polymer chain formed by any mechanism.

Examples of R in RAFT agents used in accordance with the invention also include, and in the case of R* in RAFT agents used in accordance with the invention also include a co-valent form of, optionally substituted alkyl; an optionally substituted saturated, unsaturated or aromatic carbocyclic or heterocyclic ring; optionally substituted alkylthio; optionally substituted dialkylamino; an organometallic species; and an optionally substituted polymer chain formed by any polymerisation mechanism.

More specific examples of R in RAFT agents used in accordance with the invention include optionally substituted, and in the case of R* in RAFT agents used in accordance with the invention include a m-valent form of optionally substituted, $C_1$-$C_{18}$ alkyl, $C_2$-$C_{18}$ alkenyl, $C_2$-$C_{18}$ alkynyl, $C_6$-$C_{18}$ aryl, $C_1$-$C_{18}$ acyl, $C_3$-$C_{18}$ carbocyclyl, $C_2$-$C_{18}$ heterocyclyl, $C_3$-$C_{18}$ heteroaryl, $C_1$-$C_{18}$ alkylthio, $C_2$-$C_{18}$ alkenylthio, $C_2$-$C_{18}$ alkynylthio, $C_6$-$C_{18}$ arylthio, $C_1$-$C_{18}$ acylthio, $C_3$-$C_{18}$ carbocyclylthio, $C_2$-$C_{18}$ heterocyclylthio, $C_3$-$C_{18}$ heteroarylthio, $C_3$-$C_{18}$ alkylalkenyl, $C_3$-$C_{18}$ alkylalkynyl, $C_7$-$C_{24}$ alkylaryl, $C_2$-$C_{18}$ alkylacyl, $C_4$-$C_{18}$ alkylcarbocyclyl, $C_3$-$C_{18}$ alkylheterocyclyl, $C_4$-$C_{18}$ alkylheteroaryl, $C_2$-$C_{18}$ alkyloxyalkyl, $C_3$-$C_{18}$ alkenyloxyalkyl, $C_3$-$C_{18}$ alkynyloxyalkyl, $C_7$-$C_{24}$ aryloxyalkyl, $C_2$-$C_{18}$ alkylacyloxy, $C_2$-$C_{18}$ alkylthioalkyl, $C_3$-$C_{18}$ alkenylthioalkyl, $C_3$-$C_{18}$ alkynylthioalkyl, $C_7$-$C_{24}$ arylthioalkyl, $C_2$-$C_{18}$ alkylacylthio, $C_4$-$C_{18}$ alkylcarbocyclylthio, $C_3$-$C_{18}$ alkylheterocyclylthio, $C_4$-$C_{18}$ alkylheteroarylthio, $C_4$-$C_{18}$ alkylalkenylalkyl, $C_4$-$C_{18}$ alkylalkynylalkyl, $C_8$-$C_{24}$ alkylarylalkyl, $C_3$-$C_{18}$ alkylacylalkyl, $C_{13}$-$C_{24}$ arylalkylaryl, $C_{14}$-$C_{24}$ arylalkenylaryl, $C_{14}$-$C_{24}$ arylalkynylaryl, $C_{13}$-$C_{24}$ arylacylaryl, $C_7$-$C_{18}$ arylacyl, $C_9$-$C_{18}$ arylcarbocyclyl, $C_8$-$C_{18}$ arylheterocyclyl, $C_9$-$C_{18}$ arylheteroaryl, $C_8$-$C_{18}$ alkenyloxyaryl, $C_8$-$C_{18}$ alkynyloxyaryl, $C_{12}$-$C_{24}$ aryloxyaryl, alkylthioaryl, $C_8$-$C_{18}$ alkenylthioaryl, $C_8$-$C_{18}$ alkynylthioaryl, $C_{12}$-$C_{24}$ arylthioaryl, $C_7$-$C_{18}$ arylacylthio, $C_9$-$C_{18}$ arylcarbocyclylthio, $C_8$-$C_{18}$ arylheterocyclylthio, $C_9$-$C_{18}$ arylheteroarylthio, and an optionally substituted polymer chain formed by any mechanism having a number average degree of polymerisation in the range of 2 to 5000, for example 5 to 2000, or 5 to 1000.

Where R in RAFT agents used in accordance with the invention include, and in the case of R* in RAFT agents used in accordance with the invention include a m-valent form of, an optionally substituted polymer chain formed by any mechanism, the polymers chains may be formed by chain polymerization processes such as radical, anionic, coordination polymerization or by step-growth or condensation polymerization processes. The polymer chains may comprise homopolymer, block polymer, multiblock polymer, gradient copolymer, or random or statistcal copolymer chains and may have various architectures such as linear, star, branched, graft, or brush.

Examples of polymer chains include polyesters, polyethers, polyarylenes, polyarylenevinylenes, polyfullerenes, polythiophenes, polyamides, peptides, proteins, oligonucleotides, polysiloxanes, polysilanes, polysaccharides, and polyolefins.

Still more specific goups from which R or R* may be sleeted include primary and secondary cyanoalkyls such as cyanomethyl, 1-cyanoethyl, 2-cyanopropan-2-yl, primary and secondary alkoxylcarbonylalkyls such as ethoxycarbonylmethyl, 1-ethoxycarbonylethyl and primary and secondary carboxyalkyls, tertiary cyanoalkyls such as 2-cyanobutan-2-yl, 1-cyanocyclohexyl, 2-cyano-4-methylpentan-2-yl, 2-cyano-4-methoxy-4-methylpentan-2-yl, 2-cyano-4-carboxybutan-2-yl, 2-cyano-5-hydroxypentan-2-yl, secondary cyano(aryl)alkyls such as cyano(phenyl)methyl, tertiary alkoxylcarbonylalkyls such as 2-alkoxycarbonylpropan-2-yl, 1-(butylamino)-2-methyl-1-oxopropan-2-yl, tertiary carboxyalkyls, secondary aryl(alkoxylcarbonyl)alkyls such as phenyl(ethoxycarbonyl)methyl, and other tertiary radicals such as 1-(cyclohexylamino)-2-methyl-1-oxopropan-2-yl, 1-(2-hydroxyethylamino)-2-methyl-1-oxopropan-2-yl, 1-(1,3-dihydroxy-2-(hydroxymethyl)propan-2-ylamino)-2-methyl-1-oxopropan-2-yl, 2-(4,5-dihydro-1H-imidazol-2-yl)propan-2-yl, and 2-(1-(2-hydroxyethyl)-4,5-dihydro-1H-imidazol-2-yl)propan-2-yl.

In the lists above defining groups from which R and R* may be selected, each alkyl, alkenyl, alkynyl, aryl, acyl, carbocyclyl, heterocyclyl, and heteroaryl moiety may be optionally substituted. For avoidance of any doubt, where a given R or R* group contains two or more of such moieties (e.g. alkylaryl), each moiety therein may be optionally substituted with one, two, three or more optional substituents as herein defined.

In the lists above defining divalent groups from which R and R* may be selected, where a given R or R* group contains two or more subgroups (e.g. [group A][group B]), the order of the subgroups are not intended to be limited to the order in which they are presented. Thus, a R or R* group with two subgroups defined as [group A][group B] (e.g. alkylaryl) is intended to also be a reference to a R or R* group with two subgroups defined as [group B][group A] (e.g. arylalkyl).

Where a R or R* group comprises an optionally substituted alkyl, alkenyl and/or alkynyl, moiety, an optional substituent includes the situation where a —$CH_2$— group in the alkyl, alkenyl or alkynyl chain is replaced by a group selected from —O—, —S—, —$NR^a$—, —C(O)— (i.e. carbonyl), —C(O)O— (i.e. ester), and —C(O)$NR^a$— (i.e. amide), where $R^a$ is selected from hydrogen, alkyl, alkenyl, alkynyl, aryl, carbocyclyl, heteroaryl, heterocyclyl, arylalkyl, and acyl.

In the lists above defining groups from which R*may be selected, reference to "a m-valent form of . . . " is intended to mean that the specified group is a m-valent radical. Thus, where m is, for example, 2, the specified group is intended to be a divalent radical. In that case, a divalent alkyl group is in effect an alkylene group (e.g. —$CH_2$—). Similarly, the divalent form of the group alkylaryl may, for example, be represented by —($C_6H_4$)—$CH_2$—, a divalent alkylarylalkyl group may, for example, be represented by —$CH_2$—($C_6H_4$)—$CH_2$—, a divalent alkyloxy group may, for example, be represented by —$CH_2$—O—, and a divalent alkyloxyalkyl group may, for example, be represented by —$CH_2$—O—$CH_2$—. Where the term "optionally substituted" is used in combination with such a m-valent group, that group may or may not be substituted or fused as herein described. Where the m-valent group comprises two or more subgroups, for example [group A][group B][group C] (e.g. alkylarylalkyl), if viable one or more of such subgroups may be optionally substituted.

Those skilled in the art will appreciate how to apply this rationale in providing for higher valent forms of R*. For example, the R* group may be a tri-valent alkylaryl moiety (e.g. trimethylenephenyl). In that case, the structure of formula (II) may be represented as the structure depicted directly below, where Y and X are as defined above:

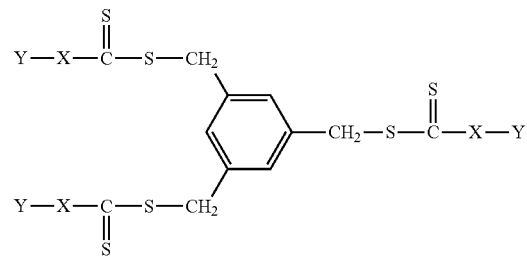

Similar considerations may of course also be applied to the n-valent form of Y.

R, R*, Y and/or Y* in the RAFT agents of the invention may be an optionally substituted polymer chain formed by any mechanism. Where R, R*, Y or Y* is an optionally substituted polymer chain, the resulting RAFT agent may conveniently be referred to as a "macro-RAFT agent".

In some embodiments of the invention, R or R* is an optionally substituted polymer chain formed by the RAFT polymerisation of one or more ethylenically unsaturated monomers. For example, a RAFT agent of formula (II) in which Y and X are as hereinbefore defined, m=1 and R*=—CH(CH₃)(COOCH₃) may be used to polymerise one or more ethylenically unsaturated monomers of formula (I) so as to afford a RAFT agent of formula (II) in the form of a macro-RAFT agent. When in the form of such a macro-RAFT agent, those skilled in the art will appreciate that the —R* moiety in formula (II) (or similarly the —R moiety in formula (III)) is intended to represent the so formed polymer chain terminally substituted with the "original" —R* (i.e. —CH(CH₃)(COOCH₃). In other words, the —R* or —R of a macro-RAFT agent is intended to embrace, and may be further defined as, —POL-R* or —POL-R, where POL is a RAFT polymerised residue of one or more ethylenically unsaturated monomers.

It may of course be possible to start with a macro-RAFT in the polymerisation of one or more ethylenically unsaturated monomers to yield a new macro-RAFT agent.

The RAFT agents of formula (II) and (III) are in some embodiments macro-RAFT agents, and these agents can be prepared by a method comprising:
(i) polymerising one or more ethylenically unsaturated monomers of formula (IV) under the control of a RAFT agent Lewis adduct of formula (V) or (VI), respectively:

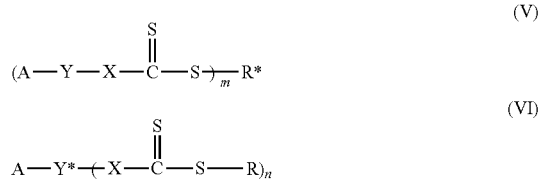

where Y, X, m and n are as defined above; Y* is an (n+1)-valent Lewis base moiety; A is a Lewis acid moiety associated with Y or Y* forming the respective adducts; R* is a m-valent radical leaving group that affords R*. which initiates free radical polymerisation of the one or more ethylenically unsaturated monomers of formula (IV); and where R is a free radical leaving group that affords R. which initiates free radical polymerisation of the one or more ethylenically unsaturated monomers of formula (IV);
to form a macro-RAFT agent Lewis adduct; and
(ii) disassociating A from Y or Y* in the so formed macro-RAFT agent Lewis adduct to thereby form the macro-RAFT agents.

For avoidance of any doubt, the term "respectively" used in step (i) immediately above is intended to indicate that the agent of formula (V) gives rise to the agent of formula (II), and the agent of formula (VI) gives rise to the agent of formula (III).

The general discussion above regarding the expression "macro-RAFT agent" also applies to macro-RAFT agent Lewis adducts. Thus, the —R or —R* of the so formed macro-RAFT agent Lewis adduct is intended to embrace, and may be defined as, —POL-R* or —POL-R, where POL is a polymerised residue of one or more ethylenically unsaturated monomers. It may of course be possible to start with a macro-RAFT agent Lewis adduct in the polymerisation of one or more ethylenically unsaturated monomers to yield a new macro-RAFT agent Lewis adduct.

After polymerising one or more ethylenically unsaturated monomers of formula (IV) under the control of a RAFT agent Lewis adduct of formula (V) or (VI) to form a macro-RAFT agent Lewis adduct, the methods of the invention may include a step of disassociating or displacing A from Y or Y* to form a macro-RAFT agent of formula (II) or (III). In other words, the bond between A and Y or Y* in the adduct can be severed to yield the Lewis base moiety Y or Y* in its free base form, thereby affording a macro-RAFT agent of formula (II) or (III).

Disassociating or displacing A from Y or Y* may be achieved by any suitable means. For example, the adduct may undergo a displacement reaction with a Lewis base having stronger Lewis basic properties than that of Y or Y. For convenience, such a Lewis base will hereinafter be referred to as a "displacing Lewis base".

The process of dissociating A from Y or Y* may therefore include introducing a displacing Lewis base to the reaction medium in which the macro-RAFT agent Lewis adduct is formed. The displacing Lewis base may be a liquid or solid and may be substantially soluble or substantially insoluble in the reaction medium.

Those skilled in the art will appreciate that by reacting the so formed macro-RAFT agent Lewis adduct with the displacing Lewis base, a new adduct between the displacing Lewis base and the Lewis acid moiety A will form, thereby liberating the macro-RAFT agent in its free base form.

If desired, the new Lewis adduct formed between the displacing Lewis base and the Lewis acid moiety can be separated from the macro-RAFT agent by any suitable means (e.g. solvent extraction and/or filtration).

Where the displacing Lewis base is a solid and substantially insoluble in the reaction medium comprising the macro-RAFT agent Lewis adduct, the reaction medium can simply be percolated through the solid displacing Lewis base so as to yield the macro-RAFT agent in free base form with the new adduct being retained in adduct formation as part the solid displacing Lewis base matrix.

Suitable displacing Lewis bases that may be used in dissociating A from Y or Y* include inorganic bases such as sodium carbonate and amine bases such as N,N-dimethylaminopyridine (DMAP). Primary or secondary amines or other bases which may react preferentially with the thiocarbonyl functionality are not preferred.

The role and function of the displacing Lewis base may be further described with reference to the RAFT agent Lewis adduct of formula (Va). Thus, upon using the adduct to control the polymerisation of one or more ethylenically unsaturated monomers of formula (IV), the so formed macro-RAFT agent Lewis adduct of formula (Vc) may subjected to a displacement reaction shown below in Scheme 3 to afford a macro-RAFT agent of formula (IIa).

Scheme 2: Displacement reaction of a macro-RAFT agent Lewis adduct of formula (Vc), where Pa is a polymerised residue of one or more ethylenically unsaturated monomers of formula (IV), with a displacing Lewis base (DMAP) to afford a macro-RAFT agent of formula (IIa) (which falls within the scope of formula (II) defined above where m = 1, X = NR$^1$ and Y = pyridyl), together with the new Lewis adduct DMAP$^+$-H.

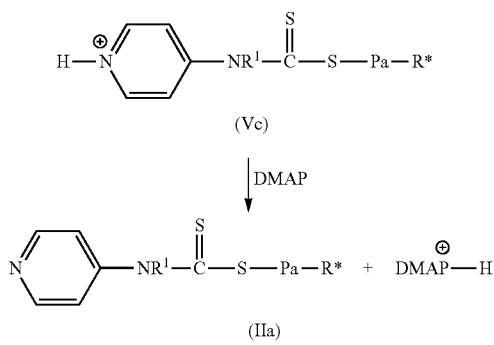

In addition to it being found that the reactivity of the adducts of formula (V) and (VI) toward free radical addition is different to their respective free base forms, it has also been found that the transition between the adduct and free base forms can be achieved efficiently and effectively without the need to isolate and/or purify the RAFT agents prior to using them in a given polymerisation reaction.

According to one aspect of the invention, a RAFT agent Lewis adduct of formula (V) or (VI) is used to polymerise monomers of formula (IV) to form a macro-RAFT agent Lewis adduct. The so formed macro-RAFT agent Lewis adduct may then be reacted with a displacing Lewis base so as to dissociate the Lewis acid moiety A from the Lewis base moiety Y or Y* of the agent to form the "free base" macro-RAFT agent. The resulting free base macro-RAFT agent can then be used to polymerise monomers of formula (I). This reaction sequence may conveniently be performed without the need to isolate and/or purify intermediate reaction products. In particular, the reaction sequence can be performed as a one pot synthesis to yield novel copolymers.

Furthermore, the RAFT agent Lewis adducts of formula (V) and (VI) may conveniently be prepared by reacting a RAFT agent of formula (IX) or (X), respectively, with a Lewis acid,

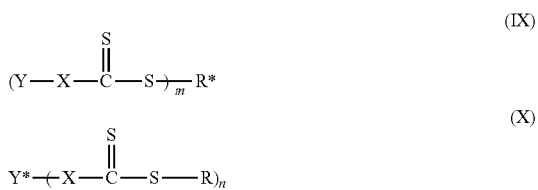

where Y, Y*, X, m and n are as defined above; R* is a m-valent radical leaving group that affords R*. which initiates free radical polymerisation of the one or more ethylenically unsaturated monomers of formula (IV); and where R is a free radical leaving group that affords R. which initiates free radical polymerisation of the one or more ethylenically unsaturated monomers of formula (IV).

Suitable Lewis acids that may be used to react with agents of formula (IX) and (X) to form the adducts include those mentioned above. In the case where the Lewis acid moiety A of formula (V) or (VI) is —H, the agents of formula (IX) or (X) may be reacted with a protic acid. Suitable protic acids include sulfonic acids such as p-toluenesulphonic acid or triflic acid (trifluoromethansulphonic acid).

The present invention therefore provides means to employ a single RAFT agent that reversibly forms a Lewis adduct to control the polymerisation of monomers having disparate reactivities so as to form unique copolymers.

The present invention therefore also provides a method of preparing polymer, the method comprising:

(i) reacting a Lewis acid moiety (A) with a RAFT agent of formula (IX) or (X),

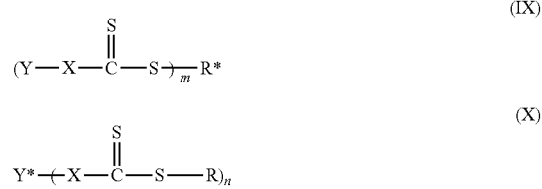

where Y is a Lewis base moiety; Y* is an n-valent Lewis base moiety; X is O or NR$^1$, R$^1$ forms together with Y or Y* and N a heterocyclic ring, or R$^1$ is independently selected from optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted arylalkyl, optionally substituted heteroarylalkyl, optionally substituted alkylaryl, optionally substituted alkylheteroaryl, and an optionally substituted polymer chain; m is an integer ≥1; n is an integer ≥2; R* is a m-valent radical leaving group that affords R*. which initiates free radical polymerisation of the one or more ethylenically unsaturated monomers of formula (IV); and where R is a free radical leaving group that affords R. which initiates free radical polymerisation of the one or more ethylenically unsaturated monomers of formula (IV), to form a RAFT agent Lewis adduct of formula (V) or (VI), respectively,

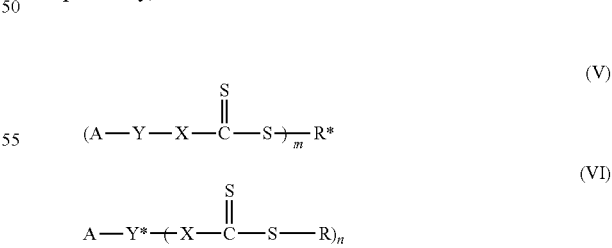

where Y, X, R, R*, m and n are as defined above; Y* is an (n+1)-valent Lewis base moiety; and where A is a Lewis acid moiety associated with Y or Y* forming the respective adducts;

(ii) polymerising one or more ethylenically unsaturated monomers of formula (IV)

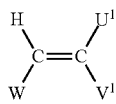

where W is H or forms together with $V^1$ a lactone, anhydride or imide ring; $U^1$ is selected from H, $C_1$-$C_4$ alkyl, $CO_2R^1$ and halogen; $V^1$ forms together with W a lactone, anhydride or imide ring, or is selected from optionally substituted aryl, alkenyl, $CO_2H$, $CO_2R^1$, $COR^1$, CN, $CONH_2$, $CONHR^1$, $CONR^1_2$, $PO(OR^1)_2$, $PO(R^1)_2$, $PO(OH)R^1$, $PO(OH)_2$, $SO(OR^1)$, $SO_2(OR^1)$, $SOR^1$ and $SO_2R^1$; and where the or each $R^1$ is as defined above, under the control of a RAFT agent Lewis adduct of formula (V) or (VI) to form a macro-RAFT agent Lewis adduct;

(iii) disassociating A from Y or Y* in the so formed macro-RAFT agent Lewis adduct to thereby form a macro-RAFT agent; and (iv) polymerising one or more ethylenically unsaturated monomers of formula (I)

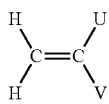

where U is selected from H, $C_1$-$C_4$ alkyl or halogen; V is halogen or of the form O-G where G is selected from —$C(O)R^1$ and —$R^1$, or V is of the form $NGG^a$ where G is as defined above and $G^a$ is selected from H and $R^1$, G and $G^a$ form together with N a heterocyclic ring, or V is of the form $CH_2G^b$ where $G^b$ is selected from H, $R^1$, OH, $OR^1$, $NR^1_2$, $PR^1_2$, $P(O)R^1_2$, $P(OR^1)_2$, $SR^1$, $SOR^1$, and $SO_2R^1$; and where the or each $R^1$ is as defined above, under the control of the macro-RAFT formed in step (iii).

RAFT agents of formula (II) or (III) may of course be used to only polymerise monomers of formula (I), and RAFT agents of formula (V) or (VI) may of course be used to only polymerise monomers of formula (IV).

Polymerisation of the monomers will usually require initiation from a source of free radicals. The source of initiating radicals can be provided by any suitable method of generating free radicals, such as the thermally induced homolytic scission of suitable compound(s) (thermal initiators such as peroxides, peroxyesters, or azo compounds), the spontaneous generation from monomers (e.g. styrene), redox initiating systems, photochemical initiating systems or high energy radiation such as electron beam, X— or gamma-radiation. The initiating system is chosen such that under the reaction conditions there is no substantial adverse interaction of the initiator or the initiating radicals with the RAFT agent under the conditions of the reaction. The initiator ideally should also have the requisite solubility in the reaction medium.

Thermal initiators are chosen to have an appropriate half life at the temperature of polymerisation. These initiators can include one or more of the following compounds:

2,2'-azobis(isobutyronitrile), 2,2'-azobis(2-cyanobutane), dimethyl 2,2'-azobis(isobutyrate), 4,4'-azobis(4-cyanovaleric acid), 1,1'-azobis(cyclohexanecarbonitrile), 2-(t-butylazo)-2-cyanopropane, 2,2'-azobis {2-methyl-N-[1,1-bis(hydroxymethyl)-2-hydroxyethyl]propionamide}, 2,2'-azobis[2-methyl-N-(2-hydroxyethyl)propionamide], 2,2'-azobis(N,N'-dimethyleneisobutyramidine)dihydrochloride, 2,2'-azobis(2-amidinopropane)dihydrochloride, 2,2'-azobis(N,N'-dimethyleneisobutyramidine), 2,2'-azobis{2-methyl-N-[1,1-bis(hydroxymethyl)-2-hydroxyethyl] propionamide}, 2,2'-azobis{2-methyl-N-[1,1-bis(hydroxymethyl)-2-ethyl]propionamide}, 2,2'-azobis[2-methyl-N-(2-hydroxyethyl)propionamide], 2,2'-azobis(isobutyramide)dihydrate, 2,2'-azobis(2,2,4-trimethylpentane), 2,2'-azobis(2-methylpropane), t-butyl peroxyacetate, t-butyl peroxybenzoate, t-butyl peroxyneodecanoate, t-butylperoxy isobutyrate, t-amyl peroxypivalate, t-butyl peroxypivalate, diisopropyl peroxydicarbonate, dicyclohexyl peroxydicarbonate, dicumyl peroxide, dibenzoyl peroxide, dilauroyl peroxide, potassium peroxydisulfate, ammonium peroxydisulfate, di-t-butyl hyponitrite, dicumyl hyponitrite. This list is not exhaustive.

Photochemical initiator systems are chosen to have the requisite solubility in the reaction medium and have an appropriate quantum yield for radical production under the conditions of the polymerisation. Examples include benzoin derivatives, benzophenone, acyl phosphine oxides, and photo-redox systems.

Redox initiator systems are chosen to have the requisite solubility in the reaction medium and have an appropriate rate of radical production under the conditions of the polymerisation; these initiating systems can include, but are not limited to, combinations of the following oxidants and reductants:

oxidants: potassium, peroxydisulfate, hydrogen peroxide, t-butyl hydroperoxide.

reductants: iron (II), titanium (III), potassium thiosulfite, potassium bisulfite.

Other suitable initiating systems are described in recent texts. See, for example, Moad and Solomon "the Chemistry of Free Radical Polymerisation", Pergamon, London, 1995, pp 53-95.

Without wishing to be limited by theory, the methods of preparing polymer according to the present invention are believed to proceed mechanistically in a similar manner to conventional methods of RAFT polymerisation. Thus, during the methods it is believed that the RAFT agent reacts with an initiating or propagating radical to give, through a RAFT-adduct radical, a new radical that initiates further polymerisation and a macro-RAFT agent having similar characteristics of the initial RAFT agent, where the R or R* group is in effect the former initiating or propagating radical (see also Scheme 1).

The reaction conditions for the polymerisation should be chosen such that the ratio of the total number of initiator-derived radicals to the number of RAFT agent molecules is maintained at a minimum value consistent with achieving an acceptable rate of polymerisation. Preferably, such a ratio is less than 1:1, more preferably less than 1:10, and most preferably in the range of 1:10 to 1:5000.

Bearing the above consideration in mind, the initiator concentration will be chosen so as to give an acceptable rate of polymerization of the specific monomer or monomer combination.

Those skilled in the art will appreciate that in the application of RAFT agents the chain transfer constant is considered an important parameter of the addition-fragmentation steps that occur in the polymerisation process. A consideration of chain transfer constants for RAFT agents is given in WO 98/01478.

Conventional techniques, conditions and reagents used in preparing polymer by RAFT polymerisation can advantageously be used in accordance with the invention. Thus, the methods of the invention may be carried out using solution, emulsion, bulk or suspension polymerisation techniques in either batch, semi-batch, continuous, or feed modes.

For heterogeneous polymerisation, it is desirable to choose a RAFT agent which has appropriate solubility parameters. For aqueous emulsion polymerisation reactions, the RAFT agent should preferably partition in favour of the organic (monomer) phase and yet have sufficient aqueous solubility that it is able to distribute between the monomer droplet phase and the polymerisation locus.

The choice of polymerisation conditions can be important. The reaction temperature may influence the rate parameters discussed above. For example, higher reaction temperatures can increase the rate of fragmentation. Conditions should be chosen such that the number of polymer chains formed from initiator-derived radicals is minimised to an extent consistent with obtaining an acceptable rate of polymerisation. Termination of polymerisation by radical-radical reaction will lead to chains which contain no active group and therefore cannot be reactivated. The rate of radical-radical termination is proportional to the square of the radical concentration. Furthermore, in the synthesis of block star or branched polymers, chains formed from initiator-derived radicals will constitute a linear homopolymer impurity in the final product. These reaction conditions therefore require careful choice of the initiator concentration and, where appropriate the rate of the initiator feed.

It is also desirable to choose other components of the reaction medium (for example, the solvents, surfactants, additives, and initiator) such that they have a low transfer constant towards the propagating radical. Chain transfer to these species will lead to the formation of polymer chains which do not contain the active RAFT group.

As a general guide in choosing conditions for the synthesis of narrow polydispersity polymers, the concentration of initiator(s) and other reaction conditions (solvent(s) if any, reaction temperature, reaction pressure, surfactants if any, other additives) should be chosen such that the molecular weight of polymer formed in the absence of the RAFT agent is at least twice that formed in its presence. In polymerisations where termination is solely by disproportionation, this equates to choosing an initiator concentration such that the total moles of initiating radicals formed during the polymerisation is less than 0.5 times that of the total moles of RAFT agent. More preferably conditions should be chosen such that the molecular weight of polymer formed in the absence of the RAFT agent is at least 5-fold that formed in its presence ([initiating radicals]/[RAFT agent]<0.2).

Thus, the polydispersity can be controlled by varying the number of moles of RAFT agent to the number of moles initiating radicals. Lower polydispersities can be obtained by increasing this ratio; higher polydispersities can be obtained by decreasing this ratio.

Polymerisation will generally be carried out at temperatures in the range of −20 to 200° C., more preferably in the range of 40 to 160° C. The polymerisation temperature will be chosen taking into consideration the specific monomer(s) being polymerised and other components of the polymerisation or reaction medium.

In the case of emulsion or suspension polymerisation the reaction medium will often be predominantly water and conventional stabilisers, dispersants and other additives may also be present.

For solution polymerisation, the reaction medium can be chosen from a wide range of media to suit the monomer(s) being used. For example, water; alcohols, such as methanol, ethanol, 2-propanol and 2-butanol; aromatic hydrocarbons, such as toluene, xylenes or petroleum naphtha; ketones, such as methyl amyl ketone, methyl isobutyl ketone, methyl ethyl ketone or acetone; esters, such as butyl acetate or hexyl acetate; ethers, such as 1,2-dimethoxyethane, tetrahydrofuran and dioxane; and glycol ether esters, such as propylene glycol monomethyl ether acetate.

The methods of the present invention involve the polymerisation of one or more ethylenically unsaturated monomers under the control of a given RAFT agent. Those skilled in the art will appreciate that the methods may also be performed using a "RAFT agent precursor" that under the reaction conditions employed forms a RAFT agent per se in the reaction medium which in turn goes on to control the polymerisation of the monomers. RAFT agent precursors referred to herein that may be used in accordance with the methods include those of formulae (II), (V) and (IX) when m=1 and R* in formula (II) and (IX) is —S—(C=S)—X—Y, or in formula (V) is —S—(C=S)—X—Y-A; or those of formula (III), (VI) and (X) when R in formula (III) and (X) is —S—(C=S)—X—Y, or in formula (VI) is —S—(C=S)—X—Y-A, where X, Y and A are as defined above.

Reagents used in performing the methods of the invention (e.g. solvents, monomers, RAFT agents, initiators etc) will of course be selected so as to not adversely interfere with the RAFT polymerisation process and/or the formation of the RAFT agent Lewis adducts.

Thus, reagents used should be chosen such that they do not comprise substituents that undergo adverse reaction with the RAFT functionality under the process conditions. For example, substituents such amino, depending on substitution pattern and reaction conditions, may undergo reaction with thiocarbonylthio compounds to cleave that group. Accordingly, primary or secondary amines, unless fully protonated, may not be preferred substituents.

The nature of the reagents used may also need to be taken into account when choosing conditions to "switch" the RAFT agent. In particular, the pKa or pKb (Lewis acidity or basicity) of the reagents used may need to be considered relative to the pKa or pKb (Lewis acidity or basicity) of the RAFT agent functionality. Examples of circumstances where this can be relevant include protonating a RAFT agent when the polymer formed comprises poly(vinylpyridine), or deprotonating a RAFT agent when the polymer formed comprises poly(methacrylic acid).

The present invention also provides a polymer comprising a moiety of formula (VII) or (VIII)

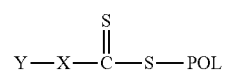

(VII)

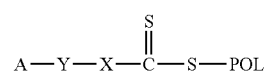

(VIII)

where Y, X, and A are as defined above; and where POL is a polymerised residue of one or more ethylenically unsaturated monomers.

The present invention also provides a polymer comprising a moiety of formula (VIIa) or (VIIIa),

(VIIa)

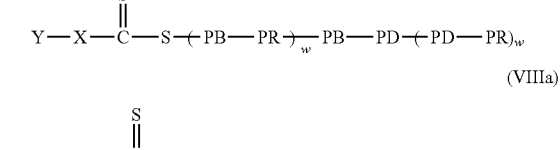
(VIIIa)

where Y, X, and A are as defined above; PB is a polymerised residue of one or more ethylenically unsaturated monomers of formula (I); PD is a polymerised residue of one or more ethylenically unsaturated monomers of formula (IV); PR is a polymerised residue of a monomer mixture formed from one or more ethylenically unsaturated monomers of formula (I) and one or more ethylenically unsaturated monomers of formula (IV); and where each w is independently 0 or 1.

The moieties of formula (VII), (VIII), (VIIa) and (VIIIa) above comprise structural elements of a polymer that may be prepared according to the present invention. The moieties may form all or part of a linear polymer, or part of a branched, star or comb polymer.

There is no particular limitation on the degree of polymerisation of any one of the polymerised monomer residues in the moieties (VII), (VIII), (VIIa) and (VIIIa) that form POL, PB, PD and PR provided that an overall polymer structure is attained. For example, PB and/or PD may be a single polymerised monomer residue. In one embodiment, the unit -PB-PD- in formula (VIIa) and (VIIIa) represents a block copolymer. Generally the degree of polymerisation of monomer residues that make up (VII), (VIII), (VIIa) or (VIIIa) will be not greater than about 5000.

Those skilled in the art will appreciate that depending upon the type of RAFT agent used and/or the type of monomer(s) polymerised, the POL, PD or PR polymerised residues may be terminally substituted with a m-valent R* moiety or an R moiety as defined above.

In some embodiments, each w in formula (VIIa) or (VIIIa) is 0. In that case, the unit -PB-PD- in formula (VIIa) and (VIIIa) will represent a block copolymer in its own right. Where at least one w in formulae (VIIa) or (VIIIa) is 1, those skilled in the art will appreciate that PR may represent a statistical copolymer formed through the RAFT polymerisation of a monomer mixture formed from one or more ethylenically unsaturated monomers of formula (I) and one or more ethylenically unsaturated monomers of (IV). In that case, the respective monomers that make up the mixture will be selected to have appropriate reactivity and mole ratios.

In preparing block copolymers according to the present invention it may be desirable to minimise the presence of monomer used in prepareing the first block during polymerisation of the monomers used to prepare a second block. For example, when preparing poly(styrene-block-vinyl acetate) it may be desirable to ensure that the amount residual styrene in the polystyrene macro RAFT agent is small or minimized since the presence of styrene monomer may inhibit or retard polymerization of vinyl acetate.

Macro RAFT agents based on monomers of formula (IV) may also act as inhibitors in the polymerization of monomers of formula (I) when the reactivity ratios are quite disparate as is the case when the monomer of formula (IV) is styrene and the monomer of formula (I) is vinyl acetate. This inhibition effect is believed to occur because the propagating radical derived from the macro RAFT agents adds to monomers of formula (I) very slowly. To minimise this inhibition effect, the block copolymers (e.g. polystyrene-block-poly(vinyl acetate)) may be prepared in a number of ways:

(a) by using higher than conventional initiator concentrations. For example, a ratio of initiator to macro RAFT agent of 1:2 may be used. This approach can be complicated by an inhibition period and the formation of dead polymer;

(b) by making a "triblock" copolymer. For example polystyrene-block-poly(methyl acrylate)-block-poly(vinyl acetate). This is a three step process but should generally yield a product of higher purity. The methyl acrylate "block" may comprise one or more monomer units; and (c) through synthesis of a gradient block copolymer. For example, as in polystyrene-block-(poly(methyl acrylate)-grad-vinyl acetate)-block-poly(vinyl acetate). This process will generally make use of monomer mixture (e.g. vinyl acetate containing a small amount of methyl acrylate) in synthesis of the second block. The process is convenient but may provide a slow rate of consumption of the macro RAFT agent. It is most suitable when a longer vinyl acetate block is required.

Examples of these synthetic strategies are provided in the Examples section.

The present invention also provides RAFT agents or RAFT agent precursors of formula (XI)-(XIV),

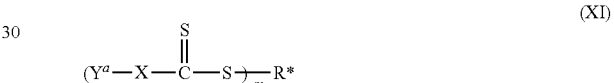
(XI)

(XII)

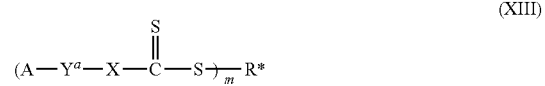
(XIII)

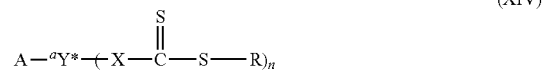
(XIV)

where X is O or $NR^1$, $R^1$ is independently selected from optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted arylalkyl, optionally substituted heteroarylalkyl, optionally substituted alkylaryl, optionally substituted alkylheteroaryl, and an optionally substituted polymer chain; R* is a co-valent radical leaving group that affords R*. which initiates free radical polymerisation of one or more ethylenically unsaturated monomers, or m in formula (XI) and (XII) is 1 and then R* in formula (XI) is —S—(C=S)—X—$Y^a$ or in formula (XIII) is —S—(C=S)—X—$Y^a$-A; R is a free radical leaving group that affords R. which initiates free radical polymerisation of one or more ethylenically unsaturated monomers, or R in formula (XII) is —S—(C=S)—X—$Y^a$ or in formula (XIV) is —S—(C=S)—X—$Y^a$-A; m is an integer ≥1; n is an integer ≥2; A is a Lewis acid moiety associated with $Y^a$ or $^aY^*$ forming the respective adducts of formula (XIII) and (XIV); and where $Y^a$ is a Lewis base moiety and $^aY^*$ is an n-valent Lewis base moiety that are each independently selected from optionally substituted heteroaryl and optionally substituted aryl-Q, where Q=NR$^1$R$^1$, SR$^1$, PR$^1$R$^1$ and SeR$^1$, and the or each R$^1$ is independently as defined above. In some embodiments, Q=NR$^1$R$^1$.

Specific RAFT agents or RAFT agent precursors of the invention and that may be used in accordance with the methods of the invention falling within the scope of RAFT agents or RAFT agent precursors of formula (XI)-(XIV) include:

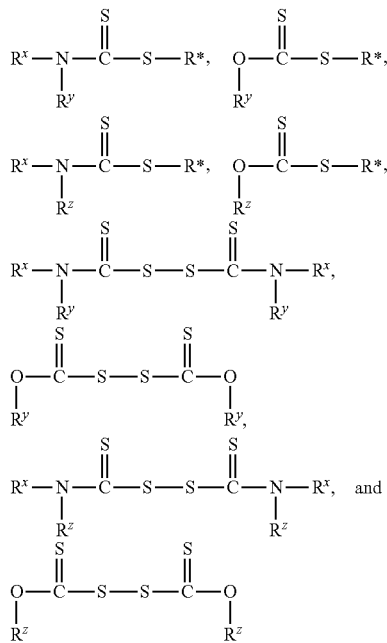

where R* is a radical leaving group that affords R*. which is capable of initiating free radical polymerisation of one or more ethylenically unsaturated monomers; R$^x$ is selected from an optionally substituted alkyl group or R$^y$; R$^y$ is an optionally substituted pyridyl group (all isomers), and R$^z$ is an optionally substituted N,N-dialkylaminophenyl group (all isomers). In some embodiments, R$^x$ is a methyl group and R$^y$ is a pyridyl group (all isomers). In some embodiments, R$^z$ is a dimethylaminophenyl group (all isomers).

In RAFT agents of formula (XI)-(XIV), or in the subset of these agent listed directly above, R or R* are preferably selected from primary and secondary cyanoalkyls such as cyanomethyl, 1-cyanoethyl, 2-cyanopropan-2-yl, primary and secondary alkoxylcarbonylalkyls such as ethoxycarbonylmethyl, 1-ethoxycarbonylethyl and primary and secondary carboxyalkyls, tertiary cyanoalkyls such as 2-cyanobutan-2-yl, 1-cyanocyclohexyl, 2-cyano-4-methylpentan-2-yl, 2-cyano-4-methoxy-4-methylpentan-2-yl, 2-cyano-4-carboxybutan-2-yl, 2-cyano-5-hydroxypentan-2-yl, secondary cyano (aryl)alkyls such as cyano(phenyl)methyl, tertiary alkoxylcarbonylalkyls such as 2-alkoxycarbonylpropan-2-yl, 1-(butylamino)-2-methyl-1-oxopropan-2-yl, tertiary carboxyalkyls, secondary aryl(alkoxylcarbonyl)alkyls such as phenyl(ethoxycarbonyl)methyl, and other tertiary radicals such as 1-(cyclohexylamino)-2-methyl-1-oxopropan-2-yl, 1-(2-hydroxyethylamino)-2-methyl-1-oxopropan-2-yl, 1-(1, 3-dihydroxy-2-(hydroxymethyl)propan-2-ylamino)-2-methyl-1-oxopropan-2-yl, 2-(4,5-dihydro-1H-imidazol-2-yl) propan-2-yl, and 2-(1-(2-hydroxyethyl)-4,5-dihydro-1H-imidazol-2-yl)propan-2-yl.

Preferred R or R* groups for controlling the polymerisation of "less activated" monomers include: primary and secondary cyanoalkyls such as cyanomethyl, 1-cyanoethyl, 2-cyanopropan-2-yl, primary and secondary alkoxylcarbonylalkyls such as ethoxycarbonylmethyl, 1-ethoxycarbonylethyl and primary and secondary carboxyalkyls.

Preferred R or R* groups for controlling the polymerisation of "more activated" monomers include: tertiary cyanoalkyls such as 2-cyanobutan-2-yl, 1-cyanocyclohexyl, 2-cyano-4-methylpentan-2-yl, 2-cyano-4-methoxy-4-methylpentan-2-yl, 2-cyano-4-carboxybutan-2-yl, 2-cyano-5-hydroxypentan-2-yl, secondary cyano(aryl)alkyls such as cyano (phenyl)methyl, tertiary alkoxylcarbonylalkyls such as 2-alkoxycarbonylpropan-2-yl, 1-(butylamino)-2-methyl-1-oxopropan-2-yl, tertiary carboxyalkyls, secondary aryl (alkoxylcarbonyl)alkyls such as phenyl(ethoxycarbonyl)methyl, and other tertiary radicals such as 1-(cyclohexylamino)-2-methyl-1-oxopropan-2-yl, 1-(2-hydroxyethylamino)-2-methyl-1-oxopropan-2-yl, 1-(1,3-dihydroxy-2-(hydroxymethyl)propan-2-ylamino)-2-methyl-1-oxopropan-2-yl, 2-(4,5-dihydro-1H-imidazol-2-yl)propan-2-yl, and 2-(1-(2-hydroxyethyl)-4,5-dihydro-1H-imidazol-2-yl)propan-2-yl.

Benzyl and substituted benzyl groups such as phenylethyl and cumyl may also be employed as R or R* groups for controlling the polymerisation of "more activated" monomers. Tertiary cyanoalkyls, secondary cyano(aryl)alkyls, secondary aryl(alkoxylcarbonyl)alkyls and cumyl are preferred R or R* groups for controlling the polymerisation of methacrylates.

As used herein, the term "alkyl", used either alone or in compound words denotes straight chain, branched or cyclic alkyl, preferably $C_{1-20}$ alkyl, e.g. $C_{1-10}$ or $C_{1-6}$ Examples of straight chain and branched alkyl include methyl, ethyl, n-propyl, isopropyl, n-butyl, sec-butyl, t-butyl, n-pentyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like. Where an alkyl group is referred to generally as "propyl", butyl" etc, it will be understood that this can refer to any of straight, branched and cyclic isomers where appropriate. An alkyl group may be optionally substituted by one or more optional substituents as herein defined.

The term "alkenyl" as used herein denotes groups formed from straight chain, branched or cyclic hydrocarbon residues containing at least one carbon to carbon double bond including ethylenically mono-, di- or polyunsaturated alkyl or cycloalkyl groups as previously defined, preferably $C_{2-20}$ alkenyl (e.g. $C_{2-10}$ or $C_{2-6}$). Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl. An alkenyl group may be optionally substituted by one or more optional substituents as herein defined.

As used herein the term "alkynyl" denotes groups formed from straight chain, branched or cyclic hydrocarbon residues containing at least one carbon-carbon triple bond including ethylenically mono-, di- or polyunsaturated alkyl or cycloalkyl groups as previously defined. Unless the number of carbon atoms is specified the term preferably refers to $C_{2-20}$ alkynyl (e.g. $C_{2-10}$ or $C_{2-6}$). Examples include ethynyl, 1-propynyl, 2-propynyl, and butynyl isomers, and pentynyl isomers. An alkynyl group may be optionally substituted by one or more optional substituents as herein defined.

The term "halogen" ("halo") denotes fluorine, chlorine, bromine or iodine (fluoro, chloro, bromo or iodo). Preferred halogens are chlorine, bromine or iodine.

The term "aryl" (or "carboaryl)" denotes any of single, polynuclear, conjugated and fused residues of aromatic hydrocarbon ring systems (e.g $C_{6-18}$ aryl). Examples of aryl include phenyl, biphenyl, terphenyl, quaterphenyl, naphthyl, tetrahydronaphthyl, anthracenyl, dihydroanthracenyl, benzanthracenyl, dibenzanthracenyl, phenanthrenyl, fluorenyl, pyrenyl, idenyl, azulenyl, chrysenyl. Preferred aryl include phenyl and naphthyl. An aryl group may or may not be optionally substituted by one or more optional substituents as herein defined. The term "arylene" is intended to denote the divalent form of aryl.

The term "carbocyclyl" includes any of non-aromatic monocyclic, polycyclic, fused or conjugated hydrocarbon residues, preferably $C_{3-20}$ (e.g. $C_{3-10}$ or $C_{3-8}$). The rings may be saturated, e.g. cycloalkyl, or may possess one or more double bonds (cycloalkenyl) and/or one or more triple bonds (cycloalkynyl). Particularly preferred carbocyclyl moieties are 5-6-membered or 9-10 membered ring systems. Suitable examples include cyclopropyl, cyclobutyl, cyclopentyl, cyclohexyl, cycloheptyl, cyclooctyl, cyclononyl, cyclodecyl, cyclopentenyl, cyclohexenyl, cyclooctenyl, cyclopentadienyl, cyclohexadienyl, cyclooctatetraenyl, indanyl, decalinyl and indenyl. A carbocyclyl group may be optionally substituted by one or more optional substituents as herein defined. The term "carbocyclylene" is intended to denote the divalent form of carbocyclyl.

The term "heterocyclyl" when used alone or in compound words includes any of monocyclic, polycyclic, fused or conjugated hydrocarbon residues, preferably $C_{3-20}$ (e.g. $C_{3-10}$ or $C_{3-8}$) wherein one or more carbon atoms are replaced by a heteroatom so as to provide a non-aromatic residue. Suitable heteroatoms include O, N, S, P and Se, particularly O, N and S. Where two or more carbon atoms are replaced, this may be by two or more of the same heteroatom or by different heteroatoms. The heterocyclyl group may be saturated or partially unsaturated, i.e. possess one or more double bonds. Particularly preferred heterocyclyl are 5-6 and 9-10 membered heterocyclyl. Suitable examples of heterocyclyl groups may include azridinyl, oxiranyl, thiiranyl, azetidinyl, oxetanyl, thietanyl, 2H-pyrrolyl, pyrrolidinyl, pyrrolinyl, piperidyl, piperazinyl, morpholinyl, indolinyl, imidazolidinyl, imidazolinyl, pyrazolidinyl, thiomorpholinyl, dioxanyl, tetrahydrofuranyl, tetrahydropyranyl, tetrahydropyrrolyl, tetrahydrothiophenyl, pyrazolinyl, dioxalanyl, thiazolidinyl, isoxazolidinyl, dihydropyranyl, oxazinyl, thiazinyl, thiomorpholinyl, oxathianyl, dithianyl, trioxanyl, thiadiazinyl, dithiazinyl, trithianyl, azepinyl, oxepinyl, thiepinyl, indenyl, indanyl, 3H-indolyl, isoindolinyl, 4H-quinolazinyl, chromenyl, chromanyl, isochromanyl, pyranyl and dihydropyranyl. A heterocyclyl group may be optionally substituted by one or more optional substituents as herein defined. The term "heterocyclylene" is intended to denote the divalent form of heterocyclyl.

The term "heteroaryl" includes any of monocyclic, polycyclic, fused or conjugated hydrocarbon residues, wherein one or more carbon atoms are replaced by a heteroatom so as to provide an aromatic residue. Preferred heteroaryl have 3-20 ring atoms, e.g. 3-10. Particularly preferred heteroaryl are 5-6 and 9-10 membered bicyclic ring systems. Suitable heteroatoms include, O, N, S, P and Se, particularly O, N and S. Where two or more carbon atoms are replaced, this may be by two or more of the same heteroatom or by different heteroatoms. Suitable examples of heteroaryl groups may include pyridyl, pyrrolyl, thienyl, imidazolyl, furanyl, benzothienyl, isobenzothienyl, benzofuranyl, isobenzofuranyl, indolyl, isoindolyl, pyrazolyl, pyrazinyl, pyrimidinyl, pyridazinyl, indolizinyl, quinolyl, isoquinolyl, phthalazinyl, 1,5-naphthyridinyl, quinoxalinyl, quinazolinyl, quinolinyl, oxazolyl, thiazolyl, isothiazolyl, isoxazolyl, triazolyl, oxadialzolyl, oxatriazolyl, triazinyl, and furazanyl. A heteroaryl group may be optionally substituted by one or more optional substituents as herein defined. The term "heteroarylene" is intended to denote the divalent form of heteroaryl.

The term "acyl" either alone or in compound words denotes a group containing the moiety C=O (and not being a carboxylic acid, ester or amide) Preferred acyl includes C(O)—$R^e$, wherein $R^e$ is hydrogen or an alkyl, alkenyl, alkynyl, aryl, heteroaryl, carbocyclyl, or heterocyclyl residue. Examples of acyl include formyl, straight chain or branched alkanoyl (e.g. $C_{1-20}$) such as acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyll; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aryloxyalkanoyl such as phenoxyacetyl and phenoxypropionyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolyglyoxyloyl and thienylglyoxyloyl. The $R^x$ residue may be optionally substituted as described herein.

The term "sulfoxide", either alone or in a compound word, refers to a group —S(O)$R^f$ wherein $R^f$ is selected from hydrogen, alkyl, alkenyl, alkynyl, aryl, heteroaryl, heterocyclyl, carbocyclyl, and aralkyl. Examples of preferred $R^y$ include $C_{1\text{-}20}$alkyl, phenyl and benzyl.

The term "sulfonyl", either alone or in a compound word, refers to a group $S(O)_2$—$R^f$, wherein $R^f$ is selected from hydrogen, alkyl, alkenyl, alkynyl, aryl, heteroaryl, heterocyclyl, carbocyclyl and aralkyl. Examples of preferred $R^y$ include $C_{1\text{-}20}$alkyl, phenyl and benzyl.

The term "sulfonamide", either alone or in a compound word, refers to a group $S(O)NR^yR^f$ wherein each $R^f$ is independently selected from hydrogen, alkyl, alkenyl, alkynyl, aryl, heteroaryl, heterocyclyl, carbocyclyl, and aralkyl. Examples of preferred $R^y$ include $C_{1\text{-}20}$alkyl, phenyl and benzyl. In a preferred embodiment at least one $R^y$ is hydrogen. In another form, both $R^y$ are hydrogen.

The term, "amino" is used here in its broadest sense as understood in the art and includes groups of the formula $NR^aR^b$ wherein $R^a$ and $R^b$ may be any independently selected from hydrogen, alkyl, alkenyl, alkynyl, aryl, carbocyclyl, heteroaryl, heterocyclyl, arylalkyl, and acyl. $R^a$ and $R^b$, together with the nitrogen to which they are attached, may also form a monocyclic, or polycyclic ring system e.g. a 3-10 membered ring, particularly, 5-6 and 9-10 membered systems. Examples of "amino" include $NH_2$, NHalkyl (e.g. $C_{1\text{-}20}$alkyl), NHaryl (e.g. NHphenyl), NHaralkyl (e.g. NHbenzyl), NHacyl (e.g. NHC(O)$C_{1\text{-}20}$alkyl, NHC(O)phenyl), Nalkylalkyl (wherein each alkyl, for example $C_{1\text{-}20}$, may be the same or different) and 5 or 6 membered rings, optionally containing one or more same or different heteroatoms (e.g. O, N and S).

The term "amido" is used here in its broadest sense as understood in the art and includes groups having the formula $C(O)NR^aR^b$, wherein $R^a$ and $R^b$ are as defined as above. Examples of amido include $C(O)NH_2$, C(O)NHalkyl (e.g. $C_{1\text{-}20}$alkyl), C(O)NHaryl (e.g. C(O)NHphenyl), C(O)NHaralkyl (e.g. C(O)NHbenzyl), C(O)NHacyl (e.g. C(O)NHC(O)$C_{1\text{-}20}$alkyl, C(O)NHC(O)phenyl), C(O)Nalkylalkyl (wherein each alkyl, for example $C_{1\text{-}20}$, may be the same or different) and 5 or 6 membered rings, optionally containing one or more same or different heteroatoms (e.g. O, N and S).

The term "carboxy ester" is used here in its broadest sense as understood in the art and includes groups having the formula $CO_2R^g$, wherein $R^g$ may be selected from groups including alkyl, alkenyl, alkynyl, aryl, carbocyclyl, heteroaryl, heterocyclyl, aralkyl, and acyl. Examples of carboxy ester include $CO_2C_{1\text{-}20}$alkyl, $CO_2$aryl (e.g. $CO_2$-phenyl), $CO_2$aralkyl (e.g. $CO_2$ benzyl).

In this specification "optionally substituted" is taken to mean that a group may or may not be substituted or fused (so as to form a condensed polycyclic group) with one, two, three or more of organic and inorganic groups, including those selected from: alkyl, alkenyl, alkynyl, carbocyclyl, aryl, heterocyclyl, heteroaryl, acyl, aralkyl, alkaryl, alkheterocyclyl, alkheteroaryl, alkcarbocyclyl, halo, haloalkyl, haloalkenyl, haloalkynyl, haloaryl, halocarbocyclyl, haloheterocyclyl, haloheteroaryl, haloacyl, haloaryalkyl, hydroxy, hydroxyalkyl, hydroxyalkenyl, hydroxyalkynyl, hydroxycarbocyclyl, hydroxyaryl, hydroxyheterocyclyl, hydroxyheteroaryl, hydroxyacyl, hydroxyaralkyl, alkoxyalkyl, alkoxyalkenyl, alkoxyalkynyl, alkoxycarbocyclyl, alkoxyaryl, alkoxyheterocyclyl, alkoxyheteroaryl, alkoxyacyl, alkoxyaralkyl, alkoxy, alkenyloxy, alkynyloxy, aryloxy, carbocyclyloxy, aralkyloxy, heteroaryloxy, heterocyclyloxy, acyloxy, haloalkoxy, haloalkenyloxy, haloalkynyloxy, haloaryloxy, halocarbocyclyloxy, haloaralkyloxy, haloheteroaryloxy, haloheterocyclyloxy, haloacyloxy, nitro, nitroalkyl, nitroalkenyl, nitroalkynyl, nitroaryl, nitroheterocyclyl, nitroheteroayl, nitrocarbocyclyl, nitroacyl, nitroaralkyl, amino ($NH_2$), alkylamino, dialkylamino, alkenylamino, alkynylamino, arylamino, diarylamino, aralkylamino, diaralkylamino, acylamino, diacylamino, heterocyclamino, heteroarylamino, carboxy, carboxyester, amido, alkylsulphonyloxy, arylsulphenyloxy, alkylsulphenyl, arylsulphenyl, thio, alkylthio, alkenylthio, alkynylthio, arylthio, aralkylthio, carbocyclylthio, heterocyclylthio, heteroarylthio, acylthio, sulfoxide, sulfonyl, sulfonamide, aminoalkyl, aminoalkenyl, aminoalkynyl, aminocarbocyclyl, aminoaryl, aminoheterocyclyl, aminoheteroaryl, aminoacyl, aminoaralkyl, thioalkyl, thioalkenyl, thioalkynyl, thiocarbocyclyl, thioaryl, thioheterocyclyl, thioheteroaryl, thioacyl, thioaralkyl, carboxyalkyl, carboxyalkenyl, carboxyalkynyl, carboxycarbocyclyl, carboxyaryl, carboxyheterocyclyl, carboxyheteroaryl, carboxyacyl, carboxyaralkyl, carboxyesteralkyl, carboxyesteralkenyl, carboxyesteralkynyl, carboxyestercarbocyclyl, carboxyesteraryl, carboxyesterheterocyclyl, carboxyesterheteroaryl, carboxyesteracyl, carboxyesteraralkyl, amidoalkyl, amidoalkenyl, amidoalkynyl, amidocarbocyclyl, amidoaryl, amidoheterocyclyl, amidoheteroaryl, amidoacyl, amidoaralkyl, formylalkyl, formylalkenyl, formylalkynyl, formylcarbocyclyl, formylaryl, formylheterocyclyl, formylheteroaryl, formylacyl, formylaralkyl, acylalkyl, acylalkenyl, acylalkynyl, acylcarbocyclyl, acylaryl, acylheterocyclyl, acylheteroaryl, acylacyl, acylaralkyl, sulfoxidealkyl, sulfoxidealkenyl, sulfoxidealkynyl, sulfoxidecarbocyclyl, sulfoxidearyl, sulfoxideheterocyclyl, sulfoxideheteroaryl, sulfoxideacyl, sulfoxidearalkyl, sulfonylalkyl, sulfonylalkenyl, sulfonylalkynyl, sulfonylcarbocyclyl, sulfonylaryl, sulfonylheterocyclyl, sulfonylheteroaryl, sulfonylacyl, sulfonylaralkyl, sulfonamidoalkyl, sulfonamidoalkenyl, sulfonamidoalkynyl, sulfonamidocarbocyclyl, sulfonamidoaryl, sulfonamidoheterocyclyl, sulfonamidoheteroaryl, sulfonamidoacyl, sulfonamidoaralkyl, nitroalkyl, nitroalkenyl, nitroalkynyl, nitrocarbocyclyl, nitroaryl, nitroheterocyclyl, nitroheteroaryl, nitroacyl, nitroaralkyl, cyano, sulfate and phosphate groups. Optional substitution may also be taken to refer to where a —$CH_2$— group in a chain or ring is replaced by a group selected from —O—, —S—, —$NR^a$—, —C(O)— (i.e. carbonyl), —C(O)O— (i.e. ester), and —C(O)$NR^a$— (i.e. amide), where $R^a$ is as defined herein.

Preferred optional substituents include alkyl, (e.g. $C_{1\text{-}6}$ alkyl such as methyl, ethyl, propyl, butyl, cyclopropyl, cyclobutyl, cyclopentyl or cyclohexyl), hydroxyalkyl (e.g. hydroxymethyl, hydroxyethyl, hydroxypropyl), alkoxyalkyl (e.g. methoxymethyl, methoxyethyl, methoxypropyl, ethoxymethyl, ethoxyethyl, ethoxypropyl etc) alkoxy (e.g. $C_{1\text{-}6}$ alkoxy such as methoxy, ethoxy, propoxy, butoxy, cyclopropoxy, cyclobutoxy), halo, trifluoromethyl, trichloromethyl, tribromomethyl, hydroxy, phenyl (which itself may be further substituted e.g., by $C_{1\text{-}6}$ alkyl, halo, hydroxy, hydroxy$C_{1\text{-}6}$ alkyl, $C_{1\text{-}6}$ alkoxy, halo$C_{1\text{-}6}$alkyl, cyano, nitro OC(O)$C_{1\text{-}6}$ alkyl, and amino), benzyl (wherein benzyl itself may be further substituted e.g., by $C_{1\text{-}6}$ alkyl, halo, hydroxy, hydroxy$C_{1\text{-}6}$alkyl, $C_{1\text{-}6}$ alkoxy, halo$C_{1\text{-}6}$ alkyl, cyano, nitro OC(O)$C_{1\text{-}6}$ alkyl, and amino), phenoxy (wherein phenyl itself may be further substituted e.g., by $C_{1\text{-}6}$ alkyl, halo, hydroxy, hydroxy$C_{1\text{-}6}$ alkyl, $C_{1\text{-}6}$ alkoxy, halo$C_{1\text{-}6}$ alkyl, cyano, nitro OC(O)$C_{1\text{-}6}$ alkyl, and amino), benzyloxy (wherein benzyl itself may be further substituted e.g., by $C_{1\text{-}6}$ alkyl, halo, hydroxy, hydroxy$C_{1\text{-}6}$ alkyl, $C_{1\text{-}6}$ alkoxy, halo$C_{1\text{-}6}$ alkyl, cyano, nitro OC(O)$C_{1\text{-}6}$alkyl, and amino), amino, alkylamino (e.g. $C_{1\text{-}6}$ alkyl, such as methylamino, ethylamino, propylamino etc), dialkylamino (e.g. $C_{1\text{-}6}$ alkyl, such as dimethylamino, diethylamino, dipropylamino), acylamino (e.g. NHC(O)$CH_3$), phenylamino (wherein phenyl itself may be further substituted e.g., by $C_{1\text{-}6}$ alkyl, halo, hydroxy, hydroxy$C_{1\text{-}6}$ alkyl, $C_{1-6}$ alkoxy, halo$C_{1-6}$ alkyl, cyano, nitro OC(O)$C_{1-6}$ alkyl, and amino), nitro, formyl, —C(O)-alkyl (e.g. $C_{1-6}$ alkyl, such as acetyl), O—C(O)-alkyl (e.g. $C_{1-6}$alkyl, such as acetyloxy), benzoyl (wherein the phenyl group itself may be further substituted e.g., by $C_{1-6}$ alkyl, halo, hydroxy hydroxy$C_{1-6}$ alkyl, $C_{1-6}$ alkoxy, halo$C_{1-6}$ alkyl, cyano, nitro OC(O)$C_{1-6}$alkyl, and amino), replacement of $CH_2$ with C=O, $CO_2$H, $CO_2$alkyl (e.g. $C_{1-6}$ alkyl such as methyl ester, ethyl ester, propyl ester, butyl ester), $CO_2$-phenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), $CONH_2$, CONHphenyl (wherein phenyl itself may be further substituted e.g., by $C_{1-6}$ alkyl, halo, hydroxy, hydroxyl $C_{1-6}$ alkyl, $C_{1-6}$ alkoxy, halo $C_{1-6}$ alkyl, cyano, nitro OC(O)$C_{1-6}$ alkyl, and amino), CONHbenzyl (wherein benzyl itself may be further substituted e.g., by $C_{1-6}$ alkyl, halo, hydroxy hydroxyl $C_{1-6}$ alkyl, $C_{1-6}$ alkoxy, halo $C_{1-6}$ alkyl, cyano, nitro OC(O)$C_{1-6}$ alkyl, and amino), CONHalkyl (e.g. $C_{1-6}$ alkyl such as methyl ester, ethyl ester, propyl ester, butyl amide) CONHdialkyl (e.g. $C_{1-6}$ alkyl)aminoalkyl (e.g., HN $C_{1-6}$ alkyl-, $C_{1-6}$alkylHN—$C_{1-6}$ alkyl- and ($C_{1-6}$ alkyl)$_2$N—$C_{1-6}$ alkyl-), thioalkyl (e.g., HS $C_{1-6}$ alkyl-), carboxyalkyl (e.g., $HO_2CC_{1-6}$ alkyl-), carboxyesteralkyl (e.g., $C_{1-6}$ alkyl$O_2CC_{1-6}$ alkyl-), amidoalkyl (e.g., $H_2N(O)CC_{1-6}$ alkyl-, H($C_{1-6}$ alkyl)N(O)$CC_{1-6}$ alkyl-), formylalkyl (e.g., OHC$C_{1-6}$alkyl-), acylalkyl (e.g., $C_{1-6}$ alkyl(O)C$C_{1-6}$ alkyl-), nitroalkyl (e.g., $O_2NC_{1-6}$ alkyl-), sulfoxidealkyl (e.g., R(O)S$C_{1-6}$ alkyl, such as $C_{1-6}$ alkyl(O)S$C_{1-6}$ alkyl-), sulfonylalkyl (e.g., R(O)$_2$S$C_{1-6}$ alkyl- such as $C_{1-6}$alkyl(O)$_2$S$C_{1-6}$ alkyl-), sulfonamidoalkyl (e.g., $_2$HRN(O)S$C_{1-6}$ alkyl, H($C_{1-6}$alkyl)N(O)S$C_{1-6}$alkyl-).

The term "heteroatom" or "hetero" as used herein in its broadest sense refers to any atom other than a carbon atom which may be a member of a cyclic organic group. Particular examples of heteroatoms include nitrogen, oxygen, sulfur, phosphorous, boron, silicon, selenium and tellurium, more particularly nitrogen, oxygen and sulfur.

For monovalent substituents, terms written as "[groupA] [group B]" refer to group A when linked by a divalent form of group B. For example, "[group A][alkyl]" refers to a particular group A (such as hydroxy, amino, etc.) when linked by divalent alkyl, i.e. alkylene (e.g. hydroxyethyl is intended to denote HO—$CH_2$—CH—). Thus, terms written as "[group] oxy" refer to a particular group when linked by oxygen, for example, the terms "alkoxy" or "alkyloxy", "alkenoxy" or "alkenyloxy", "alkynoxy" or alkynyloxy", "aryloxy" and "acyloxy", respectively, denote alkyl, alkenyl, alkynyl, aryl and acyl groups as hereinbefore defined when linked by oxygen. Similarly, terms written as "[group]thio" refer to a particular group when linked by sulfur, for example, the terms "alkylthio", "alkenylthio", alkynylthio" and "arylthio", respectively, denote alkyl, alkenyl, alkynyl and aryl groups as hereinbefore defined when linked by sulfur.

The invention will hereinafter be described with reference to the following non-limiting Examples.

EXAMPLES

General. Solvents were of AR grade and were distilled before use. Monomers, methyl acrylate (MA), butyl acrylate (BA), methyl methacrylate (MMA), styrene (S), and vinyl acetate (VAc) were obtained from Aldrich and were filtered through neutral alumina (70-230 mesh), fractionally distilled under reduced pressure, and flash distilled under reduced pressure immediately before use. N-vinylpyrrolidone (NVP) was obtained from Aldrich and was purified by vacuum distillation. N-vinylcarbazole (NVC) was obtained from Pfaltz & Bauer, Inc. and used as received. Initiators azobis(isobutyronitrile) (AIBN), azobis(cyclohexanenitrile) (ACHN) (DuPont VAZO-64® and VAZO-88® respectively) were purified by crystallization from chloroform/methanol. Gel permeation chromatography (GPC) was performed with a Waters Associates liquid chromatograph equipped with differential refractometer and 3× mixed C and 1 mixed E PLgel column (each 7.5 mm×300 mm) from Polymer Laboratories. Tetrahydrofuran (flow rate of 1.0 mL/min) was used as eluent at 22±2° C. The columns were calibrated with narrow polydispersity polystyrene standards (Polymer Laboratories). A third order polynomial was used to fit the $log_{10}M$ vs time calibration curve, which appeared approximately linear across the molecular weight range $2 \times 10^2 - 2 \times 10^6$ g $mol^{-1}$. The molecular weights in this paper are reported as polystyrene equivalents. Samples for GPC analysis were isolated by evaporation of solvent and unreacted monomer. No precipitation or fractionation was performed prior to GPC analysis. GPC of PNVP and PNVC was performed on a system comprising a Waters 590 HPLC pump and a Waters 410 refractive index detector equipped with 3× Waters Styragel columns (HT2, HT3, HT4 each 300 mm×7.8 mm providing an effective molecular weight range of 100-600000). The eluent was N,N-dimethylformamide (containing 0.045% w/v LiBr) at 80° C. (flow rate: 1 mL $min^{-1}$). Quoted monomer conversions were determined gravimetrically unless stated otherwise. The NMR spectra were recorded on a Bruker AC200 (200 MHz for $^1$H NMR) or Bruker Av400 spectrometer (400 MHz for $^1$H NMR, 125 MHz for $^{13}$C NMR) where indicated. Chemical shifts are quoted relative to (external) tetramethylsilane (TMS). High resolution electron impact (HREI) mass spectra (MS) were obtained with a ThermoQuest MAT95XP mass spectrometer employing electron impact (EI) at 70 eV and with perfluorokerosene as a reference.

Example 1

Synthesis of methyl 2-(methyl(pyridin-4-yl)carbamothioylthio) propanoate (1)

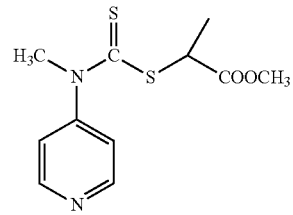

(1)

To a cold (−10° C.) solution of 4-(methylamino)pyridine (1.08 g; 10 mmol) in dry THF (60 mL) was added n-butyl lithium (1.6M in hexane) (6.25 mL, 10 mmol) over 15 minutes under an inert atmosphere. The resultant pale yellow mixture was allowed to stir at −10° C. for one hour and then warmed to 0° C. before the dropwise addition of carbon disulfide (0.9 mL); the yellow suspension was allowed to stir at room temperature overnight. Methyl 2-bromopropionate (1.23 mL, 11 mmol) was added dropwise and allowed to stir for 2 hours. THF was removed in vacuo, the mixture was suspended in ethyl acetate and filtered. After in vacuo elimination of the ethyl acetate the crude product was purified by flash chromatography using ethyl acetate as eluent to afford the title product (1), an off-white solid (2.3 g, 85.4% yield). $^1$H nmr (CDCl$_3$) δ (ppm) 1.55 (d, 3H, CHCH$_3$); 3.70 (s, 6H, COOCH$_3$ and N—CH$_3$); 4.65 (q, 1H, CHCH$_3$); 7.35 (d, 2H, m-ArH); 8.75 (br s, 2H, o-ArH).

Example 2

Synthesis of cyanomethyl methyl(pyridin-4-yl)carbamodithioate (2)

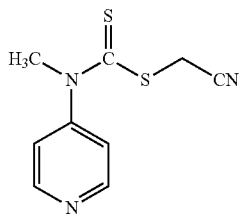

(2)

To a cold (−10° C.) solution of 4-(methylamino)pyridine (9 g, 0.0841 mol) in anhydrous THF (200 mL) was added n-butyl lithium (2.5M, 44 mL, 0.11 mol) dropwise such that the temperature remained below −7° C. The resulting pale yellow suspension was allowed to stir for about one hour at −10° C. To this mixture was added carbon disulfide (10.2 mL, 12.936 g, 0.168 mol) over one hour at 0° C. and the mixture was left to stir overnight at room temperature. The resultant mixture was cooled to 0° C. and bromoacetonitrile (8.8 mL, 15.14 g, 0.126 mol) was added dropwise. The resultant mixture was stirred at room temperature for two hours. The reaction mixture was extracted with diethyl ether (400 mL) and washed with saturated NaHCO$_3$ and brine. The organic layers were combined and dried (Na$_2$SO$_4$) and reduced to a dark brown oil. The crude was dissolved in ethyl acetate and purified by column chromatography (silica gel 60, 70-230 mesh, 30% ethyl acetate in n-hexane as eluent), gave the title compound as off-white cubes (11.05 g, 59% yield). $^1$H nmr (CDCl$_3$) δ (ppm) 3.78 (s, 3H, N—CH$_3$); 4.05 (s, 2H, SCH$_2$CN); 7.25 (m, 2H, m-ArH); 8.75 (m, 2H, o-ArH).

Example 3

Synthesis of dithiuram disulfide (3)

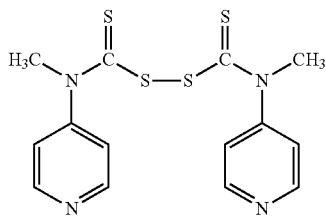

(3)

To a cold (−10° C.) solution of 4-(methylamino)pyridine (1.07 g; 9.89 mmol) in dry THF (60 mL) was added n-butyl lithium (1.6M in hexane) (6.5 mL) over 15 minutes under an inert atmosphere. The resultant pale yellow mixture was allowed to stir at −10° C. for an hour and then warm to 0° C. before the drop wise addition of carbon disulfide (0.9 mL) and the yellow suspension was allowed to stir at room temperature for further one hour. The resultant mixture was cooled to 0° C. and oxidized by the addition of an iodine solution (1.23 g iodine dissolved in 25 mL of 10% KI aqueous solution) to yield the dithiuram disulfide (3) (1.36 g, 75% yield). $^1$H nmr (CDCl$_3$) δ (ppm) 3.80 (s, 6H, 2×N—CH$_3$); 7.45 (d, 4H, m-ArH×2); 8.75 (d, 4H, o-ArH×2).

Example 4

Synthesis of 2-cyanopropan-2-yl N-methyl, N-(pyridin-4-yl)carbamodithioate (4)

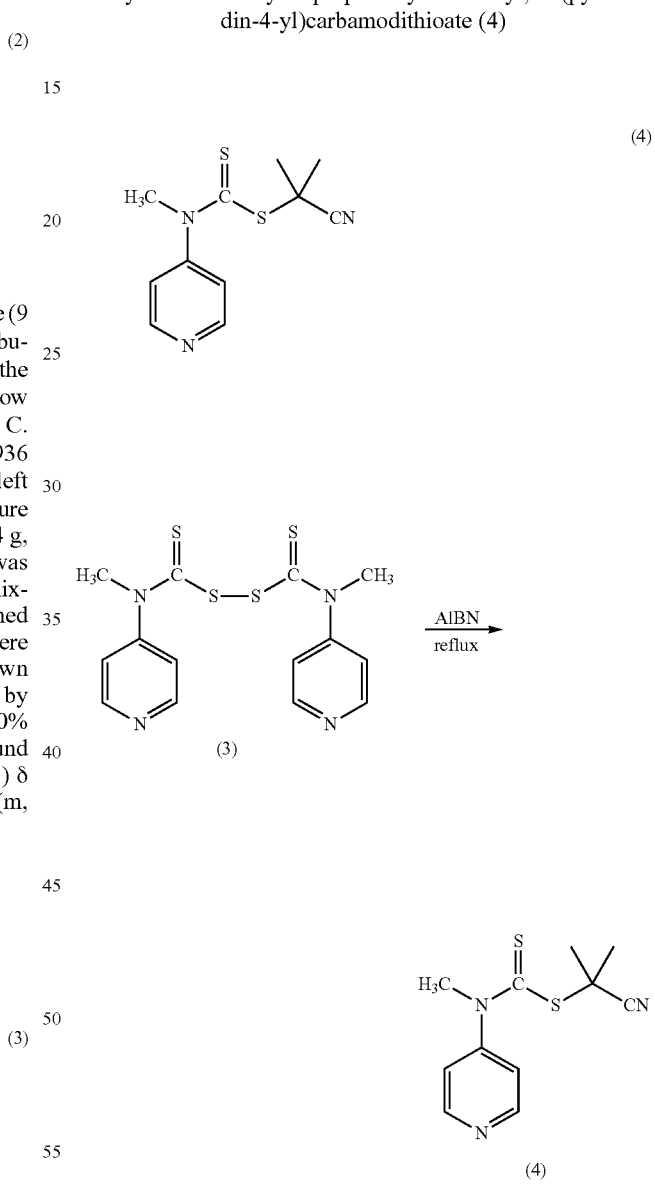

A solution of 2,2′-azobisisobutyronitrile (0.206 g, 1.26 mmol) and dithiuram disulfide (3) (0.23 g, 0.628 mmol) in ethyl acetate (10 mL) was heated at reflux for 16 h. After removal of the volatiles in vacuo, the crude product was subjected to column chromatography (Kieselgel-60, 70-230 mesh), with n-hexane:ethyl acetate (1:1) as eluant to afford 2-cyanopropan-2-yl N-methyl, N-(pyridin-4-yl)carbamodithioate (4) as an off-white liquid (0.31 g, 98.4% yield), which solidified when stored in a freezer (−15° C.). $^1$H nmr (CDCl$_3$)

δ (ppm) 1.82 (s, 6H, C(CN)(CH₃)₂); 3.65 (s, 3H, NCH₃); 7.20 (d, 2H, m-ArH); 8.75 (br.s, 2H, o-ArH).

Example 5

Synthesis of 2-cyano-4-methoxy-4-methylpentan-2-yl N-methyl, N-(pyridin-4-yl)carbamodithioate (5)

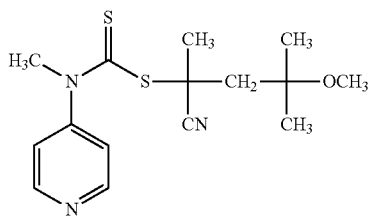

(5)

The title compound (5) was prepared according to the following Scheme:

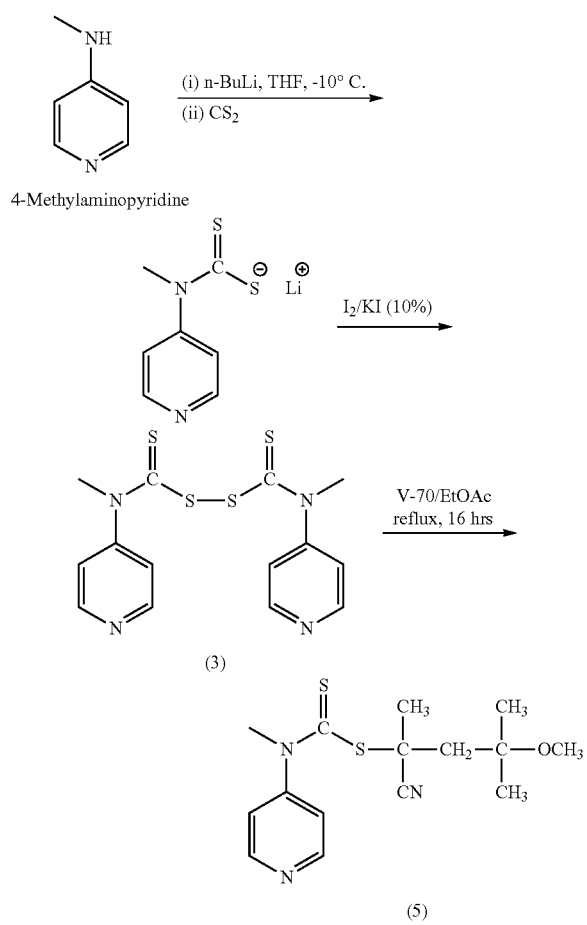

A solution of 2,2'-azobis(4-methoxy-2,4-dimethylvaleronitrile) (V-70 Wako®) (0.74 g, 2.4 mmol) and dithiuram disulfide (3) (0.73 g, 2.0 mmol) in ethyl acetate (20 mL) was heated at reflux for 16 h. After removal of the volatiles in vacuo, the crude product was subjected to column chromatography (Kieselgel-60, 70-230 mesh), with n-hexane:ethyl acetate (1:49) as eluant to afford 2-Cyano-4-methoxy-4-methylpentan-2-yl N-methyl, N-(pyridin-4-yl)carbamodithioate (5) as a pale yellow liquid (g, % yield), which solidified when stored in a freezer (−15° C.). ¹H NMR (CDCl₃) δ 1.20 (s, 3H, CH₃); 1.40 (s, 3H, CH₃); 1.85 (s, 3H, C(CN)CH₃); 1.95 (d, 1H, —CH₂—); 2.80 (d, 1H, —CH₂—); 3.10 (s, 3H, OCH₃); 3.65 (s, 3H, NCH₃); 7.30 (d, 2H, m-ArH); 8.70 (br.s, 2H, o-ArH).

Example 6

Synthesis of methyl 2-(methyl(pyridin-2-yl)carbamothioylthio)propanoate (6)

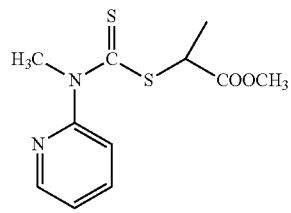

(6)

To a cold (−10° C.) solution of 2-(methylamino)pyridine (1.71 g; 15.8 mmol) in dry THF (50 mL) was added n-butyl lithium (1.6M in hexane) (10 mL, 16 mmol) over 30 minutes under an inert atmosphere. The resultant pale yellow mixture was allowed to stir at −10° C. for one hour and then warmed to 0° C. before the dropwise addition of carbon disulfide (1.58 g, 20.8 mmol); the resultant solution was allowed to stir at room temperature for one hour. Methyl 2-bromopropionate (2.84 g, 17 mmol) was added dropwise and allowed to stir for 2 hours. THF was removed in vacuo, the mixture was suspended in ethyl acetate and filtered. After in vacuo elimination of the ethyl acetate the crude product was purified by column chromatography using 20% ethyl acetate in n-hexane as eluent to afford the title product (6), an off-white solid (2.32 g, 54.3% yield). ¹H nmr (CDCl₃) δ (ppm) 1.50 (d, 3H, CHCH₃); 3.70 (s, 3H, COOCH₃ or N—CH₃); 3.75 (s, 3H, COOCH₃ or N—CH₃); 4.70 (q, 1H, CHCH₃); 7.30-7.40 (m, 2H, ArH); 7.80 (m, 1H, ArH); 8.60 (m, 1H, ArH).

Example 7

Synthesis of dithiuram disulfide (7)

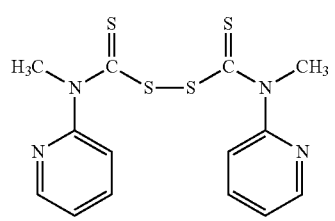

(7)

To a cold (−10° C.) solution of 2-(methylamino)pyridine (1.07 g; 0.01 mol) in dry THF (50 mL) was added n-butyl lithium (1.6M in hexane) (6.5 mL, 0.01 mol) over 30 minutes under an inert atmosphere. The mixture was allowed to stir at −10° C. for one hour and then warm to 0° C. before the dropwise addition of carbon disulfide (0.9 g) and the resulting golden color solution was allowed to stir at room temperature for further two hours. The resultant mixture was cooled to 0° C. and oxidized by the addition of an iodine solution (1.23 g iodine solid dissolved in 25 mL of 10% KI aqueous solution). Water (50 mL) was added to the reaction mixture and extracted with ethyl acetate (50 mL×3). The combined organic layers washed once with water and then dried over anhydrous MgSO$_4$. Removal of solvent on rotary evaporator gave crude product as a brownish solid, and the pure product was isolated by adding ethyl acetate/n-hexane (3:7) to the mixture, filtered and yielded the dithiuram disulfide (7) (0.74 g, 40.4% yield). $^1$H nmr (CDCl$_3$) δ (ppm) 3.85 (s, 6H, 2×N—CH$_3$); 7.35 (m, 2H, ArH); 7.65 (d, 2H, ArH); 7.85 (m, 2H, ArH); 8.60 (d, 4H, ArH).

Example 8

Synthesis of 2-Cyanopropan-2-yl N-methyl, N-(pyridin-2-yl)carbamodithioate (8)

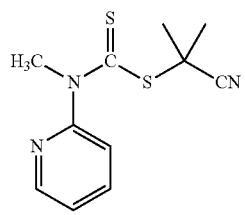

(8)

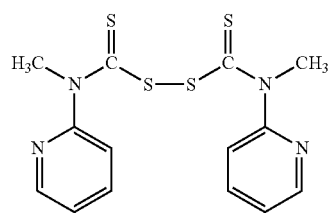

(7)

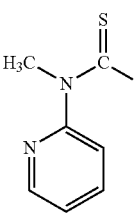

(8)

A solution of 2,2'-azobisisobutyronitrile (0.412 g, 2.51 mmol) and dithiuram disulfide (7) (0.46 g, 1.26 mmol) in ethyl acetate (30 mL) was heated at reflux for 16 h. After removal of the volatiles in vacuo, the crude product was subjected to column chromatography (Kieselgel-60, 70-230 mesh), with n-hexane:ethyl acetate (7:3) as eluent to afford 2-cyanopropan-2-yl N-methyl, N-(pyridin-2-yl)carbamodithioate (8) as an off-white liquid (0.5 g, 79% yield), which solidified when stored in a freezer (−15° C.). $^1$H nmr (CDCl$_3$) δ (ppm) 1.80 (s, 6H, C(CN)(CH$_3$)$_2$); 3.70 (s, 3H, NCH$_3$); 7.30 (m, 2H, ArH); 7.85 (m, 1H, ArH); 8.55 (m, 1H, ArH).

Example 9

Synthesis of cyanomethyl N-methyl, N-(pyridin-3-yl)carbamodithioate (9)

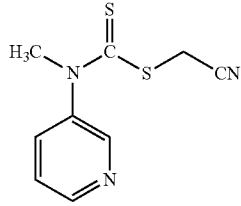

3-Methylaminopyridine is not a commercially available material.

Preparation of 3-methylaminopyridine

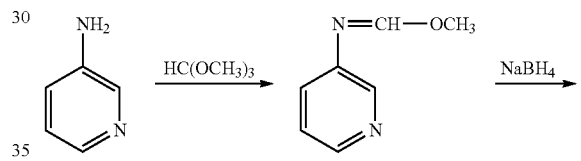

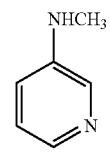

A mixture of 3-aminopyridine (7.14 g, 0.076 mol) and trimethyl orthoformate (40 mL) was refluxed for approximately 60 hr. To the cooled reaction mixture was added water (50 mL) and extracted with ethyl acetate (3×50 mL). The combined organic extracts were washed with brine and dried with MgSO$_4$. The suspension was filtered and concentrated to yield the 3-methoxyiminopyridine as a white solid (9.3 g, 90%).

$^{13}$C-NMR (CDCl$_3$): δ 51.2 (OCH$_3$); 114.3 (imine CH); 123.9; 126.5; 141.1; 144.4; 148.6 (5× pyridine C).

To a solution of the 3-methoxyiminopyridine (9.3 g, 0.068 mol) in absolute ethanol (25 mL) was added sodium borohydride (3.11 g, 0.082 mol) and the resultant suspension heated at reflux for 4 hours. The resultant mixture was cooled to room temperature and the excess NaBH$_4$.was quenched by the dropwise addition of dilute HCl. The reaction mixture was evaporated in vacuo to an oil followed by addition of water (50 mL). To the aqueous was added saturated sodium bicarbonate until pH 7, then extracted with chloroform (3×50 mL). The dried organic extracts were evaporated to give the title compound as an orange liquid (3.3 g, 40% overall).

$^1$H-NMR (CDCl$_3$): δ 3.2 (s, 3H, NCH$_3$); 7.15-7.25 (m, 1H, Ar—H); 8.0 (br s, 1H, Ar—H); 8.3 (br d, 1H, Ar—H); 8.45 (br d, 1H, Ar—H).

Preparation of S-cyanomethyl N-methyl, N-(pyridin-3-yl)carbamodithioate (9)

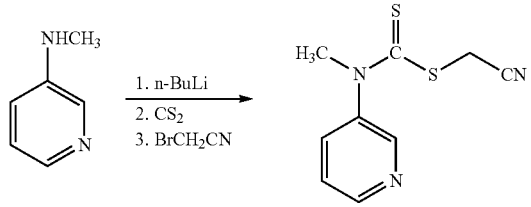

To a cold (−10° C.) solution of 3-methylaminopyridine (0.52 g; 4.84 mmol) in dry THF (10 mL) was added n-butyl lithium (2.5M, 2.3 mL) over 1 hr under an argon atmosphere. The resultant yellow/orange mixture was allowed to warm to 0° C. before the dropwise addition of carbon disulfide (0.6 ml). During the addition an exotherm was observed and the solution developed a dark red color but the temperature was not allowed to rise above 5° C. The mixture was allowed to stir at room temperature overnight. The mixture was cooled to 0° C. and bromoacetonitrile (0.7 mL) was added dropwise and then stirred at room temperature for a further 3 hrs. To this was added saturated aqueous sodium bicarbonate (20 ml) and extracted with diethyl ether (70 mL). The organic phase was washed with brine, dried over sodium sulfate and reduced to a red residue (1.3 g). Chromatography (silica using diethyl ether as eluant) gave the title compound as a yellow solid (0.7 g).

$^1$H-NMR (CDCl$_3$): δ 1.8 (s, 1H, NH); 3.8 (s, 3H, NCH$_3$); 4.05 (s, 2H, CH$_2$N); 7.5 (dd, 1H, Ar—H); 7.7 (dd, 1H, Ar—H); 8.6 (br s, 1H, Ar—H); 8.75 (br d, 1H, Ar—H). $^{13}$C-NMR (CDCl$_3$): δ 23.4; 46.4; 115.7; 124.6; 135.0; 140.0; 148.0; 150.4; 194.5.

Example 10

Synthesis of S-(methoxycarbonyl)methyl O-(4-dimethylaminophenyl)xanthate (10)

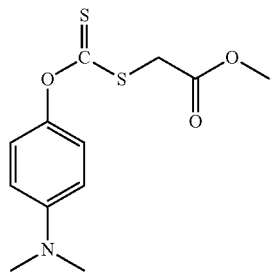

The title compound (10) was prepared through the intermediate (11) according to the following Scheme.

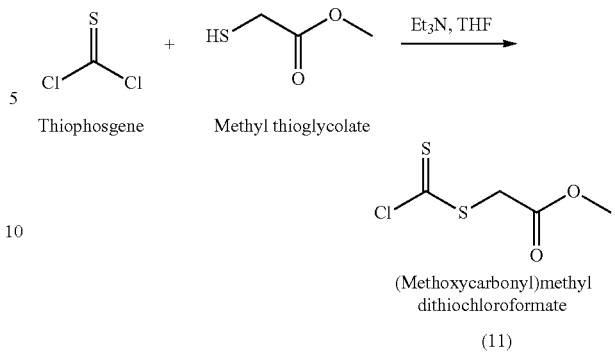

Preparation of (methoxycarbonyl)methyl dithiochloroformate intermediate (11)

To a stirred solution of excess thiophosgene (4 mL; 52.4 mmol) in anhydrous dichloromethane (40 mL) was added dropwise a solution of methyl thioglycolate (2.32 mL; 26 mmol) and triethylamine (26 mmol; 3.62 mL) in anhydrous dichloromethane (20 mL). The mixture was allowed to stir for 3 hours at room temperature, then the solvent was removed in vacuo; diethyl ether was added then the solid was filtered off. After the removal in vacuo of the volatiles, yielded (methoxycarbonyl)methyl dithiochloroformate intermediate (11) as a dark orange liquid (4.6 g; 95.7% yield). $^1$H NMR (CDCl$_3$) of (11) δ (ppm) 3.76 (s, 3H, O—CH$_3$); 4.01 (s, 2H, S—CH$_2$).

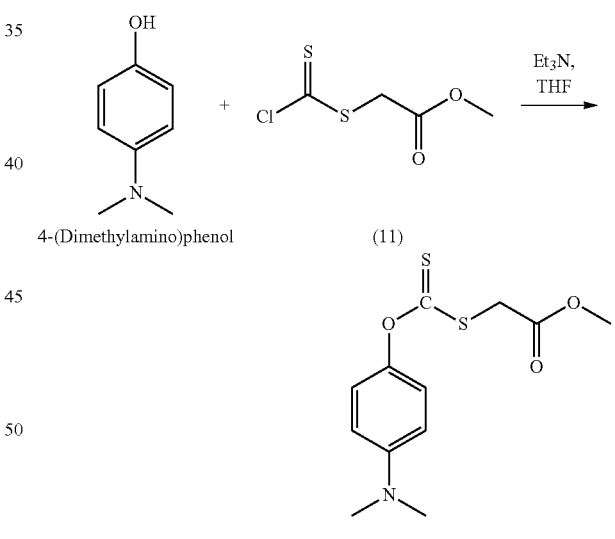

Preparation of S-(methoxycarbonyl)methyl O-(4-dimethylaminophenyl)xanthate (10)

To a stirred solution of 4-(dimethylamino)phenol (0.5 g; 3.65 mmol; *Ang. Chem. Int. Ed.* 16, 1977, 266-267) and triethylamine (0.51 mL; 3.65 mmol) in anhydrous THF (20 mL) in nitrogen atmosphere, a solution of (methoxycarbonyl) methyl dithiochloroformate (11) (0.68 g; 3.65 mmol) in anhydrous THF (10 mL) was added dropwise. After stirring for 3 hours the mixture was filtered then the solvent was removed in vacuo. The purification of the crude product by flash chromatography using dichloromethane as eluent yielded S-(methoxycarbonyl)methyl O-(4-dimethylaminophenyl) xanthate (10) as a dark yellow viscous liquid (0.51 g; 49% yield). $^1$H NMR (CDCl$_3$) of (10) δ (ppm) 2.95 (s, 6H, N—CH$_3$); 3.78 (s, 3H, O—CH$_3$); 4.04 (s, 2H, S—CH$_2$); 6.69 (d, J=9.2 Hz, 2H, m-ArH); 6.96 (d, J=9.2 Hz, 2H, o-ArH).

Example 11

Synthesis of S-benzyl O-(pyridin-4-yl)xanthate (12)

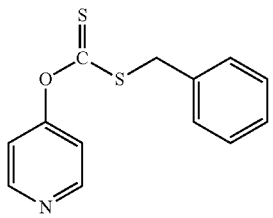

The title compound (12) was prepared according to the following Scheme:

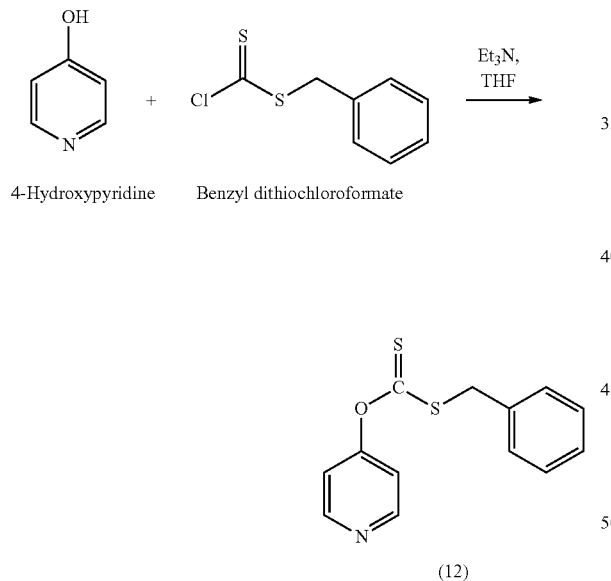

To a stirred solution of 4-hydroxypyridine (0.47 g; 4.94 mmol) and triethylamine (0.7 mL; 5 mmol) in anhydrous THF (20 mL) under nitrogen atmosphere a solution of benzyl dithiochloroformate (1 g; 4.94 mmol; Aust. J. Chem. 58, 2005, 437-441) in anhydrous THF (10 mL) was added dropwise. After stirring for 3 hours the mixture was filtered then the solvent was removed in vacuo. The purification of the crude product by flash chromatography using ethyl acetate as eluent yielded S-benzyl O-(pyridin-4-yl)xanthate (12) as a yellow crystalline solid (0.93 g; 72% yield). $^1$H NMR (CDCl$_3$) of (12) δ (ppm) 4.58 (s, 2H, S—CH$_2$); 6.33 (d, J=8.4 Hz, 2H, 3-PyH); 5.00 (m, 5H, Ar—H); 8.60 (d, J=8.4 Hz, 2H, 2-PyH).

Example 12

Synthesis of S-cyanomethyl N-(4-dimethylamino)phenyl-N'-ethyl dithiocarbamate (13)

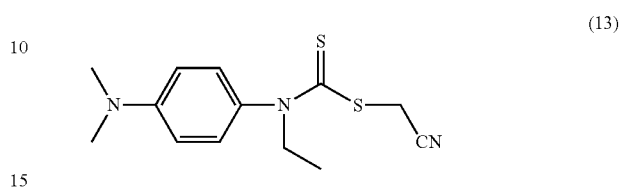

The title compound (13) was prepared according to the following reaction Scheme:

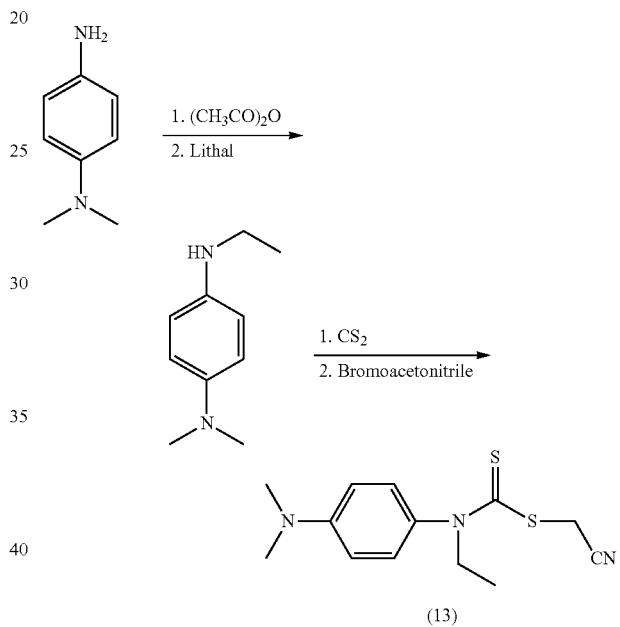

Preparation of N,N-dimethyl-N'-ethyl-1,4-phenylenediamine

To a solution of acetic anhydride (11.5 mL, 12.45 g, 0.122 mol) in anhydrous CH$_2$Cl$_2$ (100 mL) was added N,N-dimethyl-1,4-phenylenediamine (11.37 g; 83.5 mmol) portionwise over 30 min at 0° C. The mixture was allowed to gradually warm to room temperature and stirred for 24 hours. The solvent was removed under high vacuum to obtain a black residue which was stirred with Et$_2$O (20 mL) at room temperature. The suspension was filtered and the solid washed with Et$_2$O (3×20 mL). The solid residue was dried under high vacuum to obtain the intermediate N-acetyl-N',N'-dimethyl-1,4-phenylenediamine as a black solid (12.8 g, 86%) which was used in the next step without further purification.

A mixture of LiAlH$_4$ (2.87 g, 71.8 mmol) and N-acetyl-N',N'-dimethyl-1,4-phenylenediamine (from above) (12.8 g, 17.8 mol) was placed in a soxlet tube and placed in a soxlet extractor with anhydrous THF (200 mL). The mixture extracted with refluxing THF for 50 hrs. The solution was cooled to room temperature and then added wet THF at 0° C. The resultant suspension was filtered and the filtrate was evaporated under high vacuum to obtain a dark oil. The filter cake was extracted with CHCl$_3$ (2×50 mL) by stirring at room temperature. This suspension was filtered and the filtrate dried over NaSO$_4$. The solvent was evaporated to a dark oil which was combined with the other dark oil obtained from the reaction mixture. Distillation afforded the title compound, N,N-dimethyl-N'-ethyl-1,4-phenylenediamine as a yellow oil which darkened upon standing (7.84 g, 67%); b.p. 120-150° C./0.30 mmHg $^1$H-NMR (d$_6$-acetone): δ(ppm) 1.18 (m, 3H, CH$_3$); 2.80, 2.78 (2×s, 2×3H, 2×NCH$_3$); 3.05 (m, 2H, CH$_2$); 6.60-6.42 (m, 2H, ArH); 6.78-6.60 (m, 2H, ArH).

Preparation of S-cyanomethyl
N-(4-dimethylamino)phenyl-N'-ethyl
dithiocarbamate (13)

To a solution of N,N-dimethyl-N'-ethyl-1,4-phenylenediamine (2.22 g; 13.5 mmol) in dimethylsulfoxide (15 mL) was added 20M NaOH (0.81 mL) at room temperature. To this mixture was added carbon disulfide (1.62 mL, 2.06 g, 27 mmol) which produced an exotherm and the solution developed a red color. The red mixture was stirred at room temperature for 30 min and then cooled to 0° C. To this cold mixture was added 2-bromoacetonitrile (1.03 mL, 1.78 g, 14.9 mmol) dropwise. The red color was progressively discharged during the addition. The resultant mixture was stirred at room temperature for 16 hours. The orange solution was added to crush ice (50 g) and extracted with CHCl$_3$ (2×50 mL). The combined organic extracts were washed with brine (5×50 mL). The organic phase was dried over NaSO$_4$ and the solvent removed to obtain a red solid. The title compound was obtained as yellow needles (2.27 g, 60%) following chromatography on silica gel using ethyl acetate/hexane and recrystallization from Et$_2$O/hexane. m.p. 91° C.

$^1$H-NMR (CDCl$_3$): δ (ppm) 1.30 (t, 3H, CH$_3$); 3.04 (s, 6H, 2×NCH$_3$); 4.05 (s, 2H, CH$_2$); 4.30 (q, 2H, SCH$_2$CN); 6.82-6.70 (m, 2H, ArH); 7.15-7.00 (m, 2H, ArH).

In all instances, monomers were purified (to remove inhibitors) and flash-distilled immediately prior to use. The experiments referred to as controls were experiments run without the CTA unless otherwise specified. For polymerizations performed in ampoules, degassing was accomplished by repeated freeze-evacuate-thaw cycles. Once degassing was complete, the ampoules were flame sealed under vacuum and completely submerged in an oil bath at the specified temperature for the specified times. The percentage conversions were calculated gravimetrically unless otherwise indicated.

The structures of polymers and block copolymers have been verified by application of appropriate chromatographic and spectroscopic methods. Gel permeation chromatography (GPC) has been used to establish the molecular weight and molecular weight distribution (polydispersity) of the polymers. Unless otherwise specified, a Waters Associates liquid chromatograph equipped with differential refractometer and 10$^6$, 10$^5$, 10$^4$, 10$^3$, 500 and 100 Å Ultrastyragel columns was used. Tetrahydrofuran (flow rate of 1.0 mL/min) was used as eluent. The molecular weights are provided as polystyrene equivalents. The terms $M_n$, $M_w$ and $M_w/M_n$ are used to indicate the number and weight average molecular weights and the polydispersity respectively. Theoretical molecular weights [$M_n$ (calc)] were calculated according to the following expression:

$$M_n(\text{calc}) = [\text{monomer}]/[\text{CTA}] \times \text{conversion} \times \text{MWt of monomer}$$

Example 13

Preparation of low polydispersity poly(methyl methacrylate) using 2-Cyano-4-methoxy-4-methylpentan-2-yl N-methyl, N-(pyridin-4-yl)carbamodithioate (5) and trifluoromethanesulfonic acid at 60° C.

A stock solution (I) of trifluoromethanesulfonic acid (100 μL or 170 mg) in acetonitrile (5.0 mL) was prepared.

A stock solution (II) containing methyl methacrylate (7.0 mL), 2,2'-azobisisobutyronitrile (10 mg), 2-cyano-4-methoxy-4-methylpentan-2-yl N-methyl, N-(pyridin-4-yl)carbamodithioate (5) (64.3 mg, 0.0199M), acetonitrile (2.0 mL) and stock solution (I) (1.0 mL) was prepared. Aliquots (2.0 mL) of this stock solution (II) were transferred to ampoules, degassed by three repeated freeze-evacuate-thaw cycles and sealed. The ampoules were heated at 60° C. for the times indicated in the Table 1.

TABLE 1

Molecular weight and conversion data for poly(methyl methacrylate) prepared with 2-cyano-4-methoxy-4-methylpentan-2-yl N-methyl, N-(pyridin-4-yl)carbamodithioate (5) and trifluoromethanesulfonic acid at 60° C.

| Entry | time/hr | $M_n$ | $M_w/M_n$ | % Conv. |
|---|---|---|---|---|
| 1 | 3 | 1,550 | 1.42 | 3.1 |
| 2 | 6 | 5,900 | 1.36 | 12.5 |
| 3 | 16 | 31,400 | 1.10 | 65.0 |
| 4 | 40 | 48,500 | 1.18 | 98.0 |

Example 14

Preparation of low polydispersity poly(methyl methacrylate) using 2-cyanopropan-2-yl N-methyl, N-(pyridin-4-yl)carbamodithioate (4) and trifluoromethanesulfonic acid at 60° C.

A stock solution (I) of trifluoromethanesulfonic acid (100 μL or 170 mg) in acetonitrile (5.0 mL) was prepared.

A stock solution (II) containing methyl methacrylate (7.0 mL), azobisisobutyronitrile (10 mg), 2-cyanopropan-2-yl N-methyl, N-(pyridin-4-yl)carbamodithioate (4) (50.02 mg, 0.0199M), acetonitrile (2.0 mL) and stock solution (I) (1.0 mL) was prepared. Aliquots (2.0 mL) of this stock solution (II) were transferred to ampoules, degassed by three repeated freeze-evacuate-thaw cycles and sealed. The ampoules were heated at 60° C. for the times indicated in the Table 2.

TABLE 2

Molecular weight and conversion data for poly(methyl methacrylate) prepared with 2-cyanopropan-2-yl N-methyl, N-(pyridin-4-yl)carbamodithioate (4) and trifluoromethanesulfonic acid at 60° C.

| Entry | time/hr | $M_n$ | $M_w/M_n$ | % Conv. |
|---|---|---|---|---|
| 1 | 3 | 15,500 | 1.56 | 27.6 |
| 2 | 6 | 19,200 | 1.58 | 51.1 |
| 3 | 16 | 33,050 | 1.25 | 98.0 |

Example 15

Preparation of low polydispersity poly(methyl methacrylate)-b-poly(vinyl acetate)

A stock solution (I) of 2,2'-azobisisobutyronitrile (AIBN, 20.0 mg) in acetonitrile (5.0 mL) was prepared.

A yellowish solution (II) consisting of the poly(methyl methacrylate) (0.85 g) (from Example 13, entry 3; $M_n$, 31,400; $M_w/M_n$ 1.10) in acetonitrile (5.0 mL) was prepared.

Two ampoules were used and each consisted of a solution (I) (1.0 mL), solution (II) (2.0 mL) and vinyl acetate (2.0 mL) and N,N-dimethylaminopyridine (12.0 mg). A colourless solution resulted instantly. The resulting mixture was degassed, sealed and heated at 60° C. for 4 and 16 hours. The volatiles were removed in vacuo to give poly(methyl methacrylate)-b-poly(vinyl acetate) (see Table 3).

TABLE 3

Molecular weight and conversion data of poly(methyl methacrylate)-b-poly(vinyl acetate)

| Ampoule | time/hr | Weight of block copolymers (g) | $M_n$ | $M_w/M_n$ | % Conv. |
|---|---|---|---|---|---|
| 1 | 4 | 0.43 | 41,300 | 1.25 | 4.8 |
| 2 | 16 | 1.43 | 51,300 | 1.50 | 58.6 |

Example 16

Preparation of low polydispersity poly(methyl methacrylate)-b-poly(vinyl acetate)

A stock solution (I) of 2,2'-azobisisobutyronitrile (AIBN, 20.0 mg) in acetonitrile (5.0 mL) was prepared.

A yellowish solution (II) consisting of the poly(methyl methacrylate) (1.39 g) (from Example 14, entry 3; $M_n$, 33,050; $M_w/M_n$ 1.25) in acetonitrile (5.0 mL) was prepared.

Two ampoules were used and each consisted of a solution (I) (1.0 mL), solution (II) (2.0 mL) and vinyl acetate (2.0 mL) and N,N-dimethylaminopyridine (5.0 mg). A colourless solution resulted instantly. The resulting mixture was degassed, sealed and heated at 60° C. for 4 and 16 hours. The volatiles were removed in vacuo to give poly(methyl methacrylate)-b-poly(vinyl acetate) (see Table 4).

TABLE 4

Molecular weight and conversion data of poly(methyl methacrylate)-b-poly(vinyl acetate)

| Ampoule | time/hr | Weight of block copolymers (g) | $M_n$ | $M_w/M_n$ | % Conv. |
|---|---|---|---|---|---|
| 1 | 4 | 0.88 | 55,600 | 1.39 | 17.2 |
| 2 | 16 | 1.74 | 54,600 | 1.55 | 63.6 |

Example 17

Preparation of low polydispersity poly(methyl methacrylate)-b-poly(methyl acrylate)

A stock solution (I) of AIBN (8.5 mg) in acetonitrile (25.0 mL) was prepared.

A solution consisting of poly(methyl methacrylate) (1.90 g) (from Example 13, entry 3; Mn 31,400, $M_w/M_n$ 1.10) in acetonitrile (2.0 mL), stock solution (I) (1.0 mL) and methyl acrylate (2.0 mL) was prepared, which was degassed by three repeated freeze-evacuate-thaw cycles and sealed. The ampoule was heated at 70° C. for 2 hours. The volatiles were removed in vacuo to give poly(methyl methacrylate)-b-poly (methyl acrylate) at 3.30 g (73% conversion), with $M_n$ 43,970, $M_w/M_n$ 1.24.

Example 18

Preparation of low polydispersity poly(methyl methacrylate)-b-poly(methyl acrylate)-b-poly(vinyl acetate)

A stock solution (I) of AIBN (20.0 mg) in acetonitrile (5.0 mL) was prepared.

A stock solution (II) of poly(methyl methacrylate)-b-poly (methyl acrylate) (1.65 g) from Example 17 in acetonitrile (5.0 mL) was prepared.

Two ampoules were used and each consisted of a solution of (I) (1.0 mL), solution (II) (2.0 mL), N,N-dimethylaminopyridine (4.2 mg) and vinyl acetate (2.0 mL). The colour of the solution changed from yellow to colourless.

The ampoules were degassed by three repeated freeze-evacuate-thaw cycles and sealed, then heated at 60° C. for 6 and 16 hours respectively. The volatiles were removed in vacuo to give poly(methyl methacrylate)-b-poly(methyl acrylate)-b-poly(vinyl acetate) with the results summarized in the following Table 5.

TABLE 5

Molecular weight and conversion data of poly(methyl methacrylate)-b-poly(methyl acrylate)-b-poly(vinyl acetate)

| Ampoule | time/hr | Weight of block copolymers (g) | $M_n$ | $M_w/M_n$ | % Conv. |
|---|---|---|---|---|---|
| 1 | 6 | 0.73 | 50,100 | 1.30 | 3.9 |
| 2 | 16 | 1.07 | 45,500 | 1.48 | 22.0 |

Example 19

Preparation of low polydispersity poly(methyl methacrylate) using 2-cyanopropan-2-yl N-methyl, N-(pyridin-2-yl)carbamodithioate (8) and methanesulfonic acid at 60° C.

A stock solution comprising methyl methacrylate (3.5 mL), 2,2'-azobisisobutyronitrile (AIBN) (5.0 mg), 2-cyanopropan-2-yl N-methyl, N-(pyridin-2-yl)carbamodithioate (8) (30.75 mg), methanesulfonic acid (11.75 mg) and acetonitrile (1.25 mL) was prepared. Aliquots (2.0 mL) of this stock solution were transferred to ampoules, degassed by three repeated freeze-evacuate-thaw cycles and sealed. The ampoules were heated at 60° C. for the times indicated in the Table 6.

TABLE 6

Molecular weight and conversion data for poly(methyl methacrylate) prepared with 2-cyanopropan-2-yl N-methyl, N-(pyridin-2-yl)carbamodithioate (8) and methanesulfonic acid at 60° C.

| Entry | time/hr | $M_n$ | $M_w/M_n$ | % Conv. |
|---|---|---|---|---|
| 1 | 4 | 151,600 | 1.52 | 31.0 |
| 2 | 16 | 162,100 | 1.44 | 83.8 |

Example 20

Preparation of poly(methyl acrylate) using methyl 2-(methyl(pyridin-4-yl)carbamothioylthio)propanoate (1) with p-toluenesulfonic acid at 70° C.

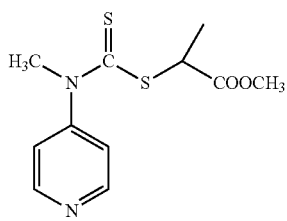

A stock solution (I) of AIBN (8.5 mg) in acetonitrile (25 mL) was prepared.

A stock solution (II) of methyl 2-(methyl(pyridin-4-yl)carbamothioylthio)propanoate (1) (47.6 mg, 0.0353M) and p-toluenesulfonic acid (38.0 mg, 0.04M) in acetonitrile (5.0 mL) was prepared.

Aliquots of stock solution (I) (1.0 mL), stock solution (II) (2.0 mL) and methyl acrylate (2.0 mL) were transferred to ampoules which were degassed by three repeated freeze-evacuate-thaw cycles and sealed. The ampoules were heated at 70° C. for the times indicated in the Table 7.

TABLE 7

Molecular weight and conversion data for poly(methyl acrylate) prepared methyl 2-(methyl(pyridin-4-yl)carbamothioylthio)propanoate (1) with p-toluenesulfonic acid at 70° C.

| Entry | time/hr | $M_n$ | $M_w/M_n$ | % Conv. |
|---|---|---|---|---|
| 1 | 2 | 20,900 | 1.09 | 58.9 |
| 2 | 7 | 31,100 | 1.08 | 87.3 |

Example 21

Preparation of low polydispersity poly(methyl acrylate)-b-poly(vinyl acetate)

A yellowish solution (I) consisting of the poly(methyl acrylate) (1.12 g) (from Example 20, entry 1; $M_n$ 20,900 $M_w/M_n$ 1.09) in acetonitrile (10 g) was prepared.

To a solution (I) (3.0 g) was added N,N-dimethylaminopyridine (3.0 mg). A colourless solution resulted instantly. To this colourless solution, AIBN (2.3 mg) and freshly distilled vinyl acetate (2.0 g) were added. The resulting mixture was degassed, sealed and heated at 60° C. for 16 hours. The volatiles were removed in vacuo to give poly(methyl acrylate)-b-poly(vinyl acetate) at 1.01 g (37% conversion based on the consumption of vinyl acetate), with $M_n$ 39,300, $M_w/M_n$ 1.25.

Example 22

Preparation of poly(n-butyl acrylate) using methyl 2-(methyl(pyridin-4-yl)carbamothioylthio)propanoate (1) with and without p-toluenesulfonic acid at 70° C.

A stock solution (I) of AIBN (8.5 mg) in acetonitrile (25 mL) was prepared.

A stock solution (II) of methyl 2-(methyl(pyridin-4-yl)carbamothioylthio)propanoate (1) (47.6 mg, 0.0353M) and p-toluenesulfonic acid (38.0 mg, 0.04M) in acetonitrile (5.0 mL) was prepared.

A stock solution (III) of methyl 2-(methyl(pyridin-4-yl)carbamothioylthio)propanoate (1) (47.6 mg, 0.0353M) in acetonitrile (5.0 mL) was prepared.

Aliquots of stock solution (I) (1.0 mL), stock solution (II) (2.0 mL) and n-butyl acrylate (2.0 mL) were transferred to ampoules (for entries 1 and 2). Aliquots of stock solution (I) (1.0 mL), stock solution (III) (2.0 mL) and n-butyl acrylate (2.0 mL) were transferred to ampoules (for entries 3 and 4).

The contents in ampoules were degassed by three repeated freeze-evacuate-thaw cycles, sealed and heated at 70° C. for the times indicated in the Table 8.

TABLE 8

Molecular weight and conversion data for poly(n-butyl acrylate) prepared methyl 2-(methyl(pyridin-4-yl)carbamothioylthio)propanoate (1) with p-toluenesulfonic acid at 70° C.

| Entry | time/hr | $M_n$ | $M_w/M_n$ | % Conv. |
|---|---|---|---|---|
| 1 | 2 | 14,300 | 1.19 | 51.7 |
| 2 | 6 | 24,150 | 1.12 | 91.9 |
| 3* | 2 | 19,800 | 1.73 | 53.7 |
| 4* | 6 | 21,250 | 1.57 | 84.3 |

*Without p-toluenesulfonic acid

Example 23

Preparation of low polydispersity poly(n-butyl acrylate)-b-poly(vinyl acetate)

A stock solution (I) of AIBN (10.1 mg) in acetonitrile (5.0 mL) was prepared.

A yellowish solution (II) consisting of the poly(n-butyl acrylate) (0.925 g) (from Example 22, entry 1; $M_n$ 14,300; $M_w/M_n$ 1.19) in acetonitrile (5.0 mL) was prepared.

To an ampoule #1, stock solution (I) (1.0 mL), yellowish solution (II) (2.0 mL) and vinyl acetate (2.0 mL) and N,N-dimethylaminopyridine (3.65 mg) were added. A colourless solution resulted instantly.

To an ampoule #2, stock solution (I) (1.0 mL), yellowish solution (II) (2.0 mL) and vinyl acetate (2.0 mL) were added.

The contents in ampoules were degassed by three freeze-evacuate-thaw cycles, sealed and heated at 60° C. for 16 hours. After removed the volatiles in vacuo, their molecular weight and conversion data are listed in Table 9. Within experimental error, the ampoule #2 showed that in the absence of base (to switch the protonated form back to the neutral form of RAFT end group) there is no block copolymer formation.

TABLE 9

Molecular weight and conversion data of poly(n-butyl acrylate)-b-poly(vinyl acetate)

| Ampoule # | time/hr | Weight of block copolymers (g) | $M_n$ | $M_w/M_n$ | % Conv. |
|---|---|---|---|---|---|
| 1 | 16 | 0.765 | 18,700 | 1.24 | 21.1 |
| 2 | 16 | 0.413 | 12,800 | 1.21 | 2.3 |

Example 24

Preparation of poly(n-butyl acrylate) using methyl 2-(methyl(pyridin-2-yl) carbamothioylthio)propanoate (6) with p-toluenesulfonic acid at 70° C.

A stock solution (I) of AIBN (8.5 mg) in acetonitrile (25 mL) was prepared.

A stock solution (II) of methyl 2-(methyl(pyridin-2-yl) carbamothioylthio)propanoate (6) (23.85 mg, 0.0177M) and p-toluenesulfonic acid (19.1 mg, 0.02M) in acetonitrile (5.0 mL) was prepared.

Aliquots of stock solution (I) (1.0 mL), stock solution (II) (2.0 mL) and n-butyl acrylate (2.0 mL) were transferred to ampoules.

The contents in ampoules were degassed by three repeated freeze-evacuate-thaw cycles, sealed and heated at 70° C. for the times indicated in the Table 10.

TABLE 10

Molecular weight and conversion data for poly(n-butyl acrylate) prepared with methyl 2-(methyl(pyridin-2-yl)carbamothioylthio)propanoate (6) with p-toluenesulfonic acid at 70° C.

| Entry | time/hr | $M_n$ | $M_w/M_n$ | % Conv. |
|---|---|---|---|---|
| 1 | 2 | 49,000 | 1.43 | 60.4 |
| 2 | 7 | 55,000 | 1.44 | 83.5 |

Example 25

Preparation of poly(n-butyl acrylate) using cyanomethyl methyl(pyridin-4-yl)carbamodithioate (2) with and without Lewis acid aluminium trifluoromethanesulfonate at 70° C.

A stock solution (I) of AIBN (8.5 mg) in acetonitrile (25 mL) was prepared.

A stock solution (II) of cyanomethyl methyl(pyridin-4-yl) carbamodithioate (2) (22.3 mg) and Lewis acid aluminium trifluoromethanesulfonate (47.4 mg) in acetonitrile (5.0 mL) was prepared.

A stock solution (III) of cyanomethyl methyl(pyridin-4-yl) carbamodithioate (2) (22.3 mg) in acetonitrile (5.0 mL) was prepared.

Aliquots of stock solution (I) (1.0 mL), stock solution (II) (2.0 mL) and n-butyl acrylate (2.0 mL) were transferred to two ampoules labelled 2A and 6A.

Aliquots of stock solution (I) (1.0 mL), stock solution (III) (2.0 mL) and n-butyl acrylate (2.0 mL) were transferred to two ampoules labelled 2B and 6B.

The contents in ampoules were degassed by three repeated freeze-evacuate-thaw cycles, sealed and heated at 70° C. for the times indicated in the Table 11.

TABLE 11

Molecular weight and conversion data for poly(n-butyl acrylate) prepared with cyanomethyl methyl(pyridin-4-yl)carbamodithioate (2) with and without Lewis acid aluminium trifluoromethanesulfonate at 70° C.

| Entry | Sample | time/hr | $M_n$ | $M_w/M_n$ | % Conv. |
|---|---|---|---|---|---|
| 1 | 2A | 2 | 31,000 | 1.16 | 59.2 |
| 2 | 6A | 6 | 47,040 | 1.14 | 84.5 |
| 3 | 2B | 2 | 51,500 | 1.74 | 65.1 |
| 4 | 6B | 6 | 51,400 | 1.88 | 84.7 |

Example 26

Preparation of low polydispersity poly(methyl acrylate) using S-benzyl O-(pyridin-4-yl)xanthate (12) and p-toluenesulfonic acid at 70° C.

A stock solution of AIBN (1.64 mg), S-benzyl O-(pyridin-4-yl)xanthate (12) (36.5 mg) p-toluenesulfonic acid (24.1 mg), methyl acrylate (4 mL) and acetonitrile to a volume of 10 mL was prepared in a volumetric flask. Aliquots (2 mL) of this stock solution were transferred to ampoules which were degassed by three repeated freeze-evacuate-thaw cycles and sealed. The ampoules were heated at 70° C. for the times indicated in the Table 12.

TABLE 12

Molecular weight and conversion data for poly(methyl acrylate) prepared with S-benzyl O-(pyridin-4-yl) Xanthate (12) and p-toluenesulfonic acid at 70° C.

| Entry | time/hr | $M_n$ | $M_w/M_n$ | % Conv. |
|---|---|---|---|---|
| 1 | 2 | 40,700 | 1.57 | 15.7 |
| 2 | 4 | 51,200 | 1.51 | 28.9 |
| 3 | 6 | 54,900 | 1.56 | 32.7 |
| 4 | 8 | 57,300 | 1.59 | 44.5 |
| 5 | 16 | 63,400 | 1.57 | 67 |

Example 27

Preparation of low polydispersity polystyrene using cyanomethyl methyl(pyridin-4-yl)carbamodithioate (2) with p-toluenesulfonic acid at 90° C.

Styrene (3 mL), VAZO-88 (5 mg), cyanomethyl methyl (pyridin-4-yl)carbamodithioate (2) (22 mg) and p-toluenesulfonic acid (18 mg) in acetonitrile (2 mL) were transferred into a test-tube ampoule which was degassed by three repeated freeze-evacuate-thaw cycles and sealed. The ampoule was heated at 90° C. for 16 hours. The un-reacted monomer was removed on rotary evaporator and gave low polydispersity polystyrene (1.57 g, 57.5% conversion). GPC results: $M_n$ 14,500; $M_w/M_n$ 1.21

Example 28

Preparation of low polydispersity polystyrene using methyl 2-(methyl(pyridin-4-yl)carbamothioylthio) propanoate (1) with p-toluenesulfonic acid at 90° C.

A stock solution of 1,1'-azobis(cyclohexanecarbonitrile) (VAZO-88) (12.2 mg), methyl 2-(methyl(pyridin-4-yl)carbamothioylthio)propanoate (1) (27 mg), p-toluenesulfonic acid (17.2 mg) and styrene was prepared in a 10 mL volumetric flask. Aliquots (2.0 mL) of this stock solution were transferred to ampoules which were degassed by three repeated freeze-evacuate-thaw cycles and sealed. The ampoules were heated at 90° C. for the times indicated in the Table 13.

TABLE 13

Molecular weight and conversion data for polystyrene prepared with methyl 2-(methyl(pyridin-4-yl)carbamothioylthio)propanoate (1) and p-toluenesulfonic acid at 90° C.

| Entry | time/hr | $M_n$ | $M_w/M_n$ | % Conv. |
|---|---|---|---|---|
| 1 | 4.5 | 26,000 | 1.12 | 34.8 |
| 2 | 9 | 40,000 | 1.13 | 57.2 |
| 3 | 16 | 56,000 | 1.14 | 77.4 |
| 4 | 22 | 63,000 | 1.17 | 95.7 |

Example 29

Preparation of Low Polydispersity and Low Molecular Weight Polystyrene Using Methyl 2-(methyl(pyridin-4-yl)carbamothioylthio)propanoate (1) and p-toluenesulfonic acid at 90° C.

Three ampoules were used and each containing a solution of 1,1' azobis(cyclohexanecarbonitrile) (VAZO-88) (12.2 mg), methyl 2-(methyl(pyridin-4-yl)carbamothioylthio)propanoate (1) (94.5 mg), p-toluenesulfonic acid (60.2 mg) and styrene (5 mL). The ampoules, after degassed by three repeated freeze-evacuate-thaw cycles, were sealed and heated at 90° C. for the times indicated in the Table 14.

TABLE 14

Molecular weight and conversion data for polystyrene prepared with methyl 2-(methyl(pyridin-4-yl)carbamothioylthio)propanoate (1) and p-toluenesulfonic acid at 90° C.

| Entry | time/hr | $M_n$ | $M_w/M_n$ | % Conv. |
|---|---|---|---|---|
| 1 | 2 | 1,800 | 1.33 | 19.5 |
| 2 | 6 | 6,000 | 1.08 | 47.2 |
| 3 | 12 | 10,500 | 1.06 | 81.6 |

Example 30

Preparation of low polydispersity polystyrene using 2-cyanopropan-2-yl N-methyl, N-(pyridin-4-yl)carbamodithioate (4) with p-toluenesulfonic acid at 90° C.

An experiment carried out under the same conditions similar to those used in Example 27 with the exception of 2-cyanopropan-2-yl N-methyl, N-(pyridin-4-yl)carbamodithioate (4) (25.1 mg) as RAFT agent, gave low polydispersity polystyrene (0.99 g, 36.4% conversion). GPC results: $M_n$ 10,800; $M_w/M_n$ 1.30.

Example 31

Preparation of low polydispersity polystyrene-b-poly(vinyl acetate)

The polystyrene sample was dissolved in dichloromethane and percolated through a carefully crushed and dried sodium carbonate bed before use. The colour of the solution changed from yellow to colourless. Removal of the solvent gave the polystyrene ready to be used as follows.

A solution consisting of polystyrene (0.178 g) (from Example 29, entry 1; Mn 1,800, $M_w/M_n$ 1.33), AIBN (8.2 mg) and vinyl acetate to a volume of 10 mL (9.025 g) was prepared. Aliquots (2.0 mL) of this solution were transferred to ampoules which were degassed by three repeated freeze-evacuate-thaw cycles and sealed. The ampoules were heated at 70° C. for the times indicated in the Table 15. The volatiles were removed in vacuo to give polystyrene-b-poly(vinyl acetate). The NMR regions between 4.6-5.2 ppm (pVA) and 6.2-7.4 ppm (pSt) were considered to calculate the $^{NMR}$Mn.

TABLE 15

Molecular weight and conversion data for polystyrene-b-poly(vinyl acetate) at 70° C.

| Entry | time/hr | $M_n$ | $^{NMR}M_n$ | $^{Calc.}M_n$ | $M_w/M_n$ | % Conv. |
|---|---|---|---|---|---|---|
| 1 | 4 | 6,000 | 8,000 | 8,700 | 2.70 | 7.4 |
| 2 | 6 | 29,000 | 19,000 | 21,000 | 1.39 | 21.0 |
| 3 | 8 | 43,000 | 29,000 | 33,000 | 1.40 | 34.3 |
| 4 | 12 | 58,000 | 43,000 | 50,000 | 1.58 | 53.1 |

Example 32

Preparation of low polydispersity polystyrene-b-poly(methyl acrylate)

A solution consisting of polystyrene (0.56 g) (from Example 29, entry 3; Mn 10,500, $M_w/M_n$ 1.06), AIBN (8.2 mg), methyl acrylate (2.5 mL) and benzene (2 mL, total volume 5 mL) was prepared in an ampoule which was degassed by three repeated freeze-evacuate-thaw cycles and sealed. The ampoule was heated at 70° C. for 3 hours. The volatiles were removed in vacuo to give poly(styrene)-b-poly(methyl acrylate) at 1.15 g (24.6%), with $M_n$ 21,500, $M_w/M_n$ 1.15. The $^{NMR}$Mn 22,000 was calculated considering the NMR regions between 3.2-4.0 ppm (pMA) and 6.2-7.4 ppm (pSt).

Example 33

Preparation of low polydispersity poly(styrene)-b-poly(methyl acrylate)-b-poly(vinyl acetate)

The poly(styrene)-b-poly(methyl acrylate) sample from Example 32 was dissolved in dichloromethane and percolated through a carefully crushed and dried sodium carbonate bed before use. The colour of the solution changed from yellow to colourless. Removal of the solvent gave the poly(styrene)-b-poly(methyl acrylate) ready to be used as follows.

A solution consisting of poly(styrene)-b-poly(methyl acrylate) from Example 32 (0.5 g) ($^{NMR}$Mn 21,500, Mw/Mn 1.15), AIBN (1.64 mg) and vinyl acetate (1.65 mL) was prepared in an ampoule which was degassed by three repeated freeze-evacuate-thaw cycles and sealed. The ampoule was heated at 70° C. for 15 hours. The volatiles were removed in vacuo to give poly(styrene)-b-poly(methyl acrylate)-b-poly (vinyl acetate) at 1.60 g (73.6%), with $M_n$ 52,000, $M_w/M_n$ 1.48. The $^{NMR}$Mn 72,000 was calculated considering the NMR regions between 4.6-5.2 ppm (pVA) and 6.2-7.4 ppm (pSt).

Example 34

Preparation of low polydispersity poly(vinyl acetate) using methyl 2-(methyl(pyridin-4-yl)carbamothioylthio)propanoate (1) at 60° C.

Vinyl acetate (5.0 mL), AIBN (5.1 mg) and methyl 2-(methyl(pyridin-4-yl)carbamothioylthio)propanoate (1) (59.44 mg) were transferred into a test-tube ampoule which was degassed by three repeated freeze-evacuate-thaw cycles and sealed. The ampoule was heated at 60° C. for 4 hours. After the reaction, the un-reacted monomer was removed on rotary evaporator and gave low polydispersity poly(vinyl acetate) (1.52 g, 32.6% conversion). GPC results: $M_n$ 8,400; $M_w/M_n$ 1.25.

Example 35

Preparation of low polydispersity poly(vinyl acetate) using s-cyanomethyl n-methyl, N-(pyridin-3-yl)carbamodithioate (9) at 75° C.

A stock solution of VAZO-88 (10.3 mg), vinyl acetate (10 mL) and ethyl acetate (5.0 mL) was prepared.

Aliquot (3.0 mL) of this stock solution was transferred into an ampoule containing S-cyanomethyl N-methyl, N-(pyridin-3-yl)carbamodithioate (9) (35.0 mg) which was degassed by three repeated freeze-evacuate-thaw cycles and sealed. The ampoule was heated at 75° C. for 3 days. After the reaction, the un-reacted monomer was removed on rotary evaporator and gave low polydispersity poly(vinyl acetate) (54.8% conversion). GPC results: $M_n$ 8,900; $M_w/M_n$ 1.24.

Example 36

Preparation of low polydispersity poly(vinyl acetate) using s-(methoxycarbonyl)methyl O-(4-dimethylaminophenyl)xanthate (10) at 70° C.

A stock solution of AIBN (2.5 mg), S-(methoxycarbonyl)methyl O-(4-dimethylaminophenyl)xanthate (10) (39.8 mg) and vinyl acetate to a volume of 10 mL was prepared in a volumetric flask. Aliquots (2.5 mL) of this stock solution were transferred to ampoules which were degassed by three repeated freeze-evacuate-thaw cycles and sealed. The ampoules were heated at 70° C. for the times indicated in the Table 16.

TABLE 16

Molecular weight and conversion data for poly(vinyl acetate) prepared with S-(methoxycarbonyl)methyl O-(4-dimethylaminophenyl) xanthate (10) at 70° C.

| Entry | time/hr | $M_n$ | $M_w/M_n$ | % Conv. |
|---|---|---|---|---|
| 1 | 16 | 14,400 | 1.20 | 13.9 |
| 2 | 23 | 25,800 | 1.37 | 29.9 |

Example 37

Preparation of low polydispersity poly(vinyl acetate) using s-(methoxycarbonyl)methyl O-(4-dimethylaminophenyl)xanthate (10) at 80° C.

A stock solution of AIBN (1.8 mg), S-(methoxycarbonyl)methyl O-(4-dimethylaminophenyl)xanthate (10) (28.3 mg), vinyl acetate (7 mL) and benzene to a volume of 10 mL was prepared in a volumetric flask. Aliquots (2.5 mL) of this stock solution were transferred to ampoules which were degassed by three repeated freeze-evacuate-thaw cycles and sealed. The ampoules were heated at 80° C. for the times indicated in the Table 17.

TABLE 17

Molecular weight and conversion data for poly(vinyl acetate) prepared with S-(methoxycarbonyl)methyl O-(4-dimethylaminophenyl) xanthate (10) at 80° C.

| Entry | time/hr | $M_n$ | $M_w/M_n$ | % Conv. |
|---|---|---|---|---|
| 1 | 8 | 28,000 | 1.37 | 31.4 |
| 2 | 16 | 32,500 | 1.39 | 42 |

Example 38

Preparation of low polydispersity poly(vinyl acetate) using S-cyanomethyl N,N-dimethyl-N'-ethyl-1,4-phenylenediamine dithiocarbamate (13) at 75° C.

A stock solution of VAZO-88 (10.1 mg), vinyl acetate (10 mL) and ethyl acetate (5.0 mL) was prepared.

Aliquot (3.0 mL) of this stock solution was transferred into an ampoule containing S-cyanomethyl N,N-dimethyl-N'-ethyl-1,4-phenylenediamine dithiocarbamate (13) (41.5 mg) which was degassed by three repeated freeze-evacuate-thaw cycles and sealed. The ampoule was heated at 75° C. for 89 hours. After the reaction, the un-reacted monomer was removed on rotary evaporator and gave low polydispersity poly(vinyl acetate) (22.3% conversion). GPC results: $M_n$ 3,070; $M_w/M_n$ 2.03.

Example 39

Preparation of low polydispersity poly(N-vinyl pyrrolidone) using methyl 2-(methyl(pyridin-4-yl)carbamothioylthio)propanoate (1) at 60° C.

A stock solution (I) comprising of AIBN (10.0 mg) in acetonitrile (5 mL) was prepared.

N-vinyl pyrrolidone (2.0 mL), stock solution (I) (1.0 mL) and methyl 2-(methyl(pyridin-4-yl)carbamothioylthio)propanoate (1) (13.5 mg) in acetonitrile (1.0 mL) were transferred into a test-tube ampoule which was degassed by three repeated freeze-evacuate-thaw cycles and sealed. The ampoule was heated at 60° C. for 16 hours. After the reaction, removed the organic solvent, and the residue was added slowly into ethyl acetate (200 mL) to isolate low polydispersity poly(N-vinyl pyrrolidone) (1.73 g, 82.9% conversion). GPC (in DMF) results: $M_n$ 29,400; $M_w/M_n$ 1.19

Example 40

Preparation of low polydispersity poly(N-vinyl carbazole) using methyl 2-(methyl(pyridin-4-yl)carbamothioylthio)propanoate (1) at 60° C.

N-vinyl carbazole (0.5 g), AIBN (2.0 mg) and methyl 2-(methyl(pyridin-4-yl)carbamothioylthio)propanoate (1) (5.0 mg) in 1,4-dioxane (0.75 mL) were transferred into a test-tube ampoule which was degassed by three repeated freeze-evacuate-thaw cycles and sealed. The ampoule was heated at 60° C. for 20 hours. After the reaction, the reaction mixture was added slowly into n-hexane (150 mL) to isolate low polydispersity poly(N-vinyl carbazole) (0.398 g, 79.7% conversion). GPC (DMF as eluent) results: $M_n$ 15,800; $M_w/M_n$ 1.09

Example 41

Preparation of low polydispersity poly(n-vinyl carbazole)-b-poly(vinyl acetate)

A sample of poly(N-vinyl carbazole) (0.15 g) from Example 37 above was dissolved in 1,4-dioxane (1.0 mL) and transferred into an ampoule containing AIBN (2.0 mg) and vinyl acetate (0.5 mL). The resulting mixture was degassed by three repeated freeze-thaw-evacuate cycles, sealed and heated at 70° C. for 3 hours. The volatiles were removed in vacuo to give poly(N-vinyl carbazole)-b-poly(vinyl acetate) at 0.4 g (53.5% conversion based on consumption of vinyl acetate), with GPC (DMF as eluent) result: $M_n$ 20,850, $M_w/M_n$ 1.24.

Example 42

Preparation of low polydispersity poly(methyl acrylate)-b-poly(n-vinyl carbazole)

A stock solution (I) consisting of the poly(methyl acrylate) (1.67 g) (from Example 20, entry 2; $M_n$ 31,100; $M_w/M_n$ 1.08), N,N-dimethylaminopyridine (10.0 mg) in acetonitrile (10 mL) was prepared.

A stock solution (II) of AIBN (10 mg) in acetonitrile (5 mL) was prepared.

N-vinyl carbazole (0.5 g), stock solution (I) (2.0 mL), stock solution (II) (1.0 mL) and acetonitrile (1.0 mL) were transferred into a test-tube ampoule which was degassed by three repeated freeze-evacuate-thaw cycles and sealed. The ampoule was heated at 60° C. for 16 hours. The volatiles were removed in vacuo to give poly(methyl acrylate)-b-poly(N-vinyl carbazole) (almost complete conversion of N-vinyl carbazole based on $^1$H-nmr) with GPC (in THF) result: $M_n$ 48,000, $M_w/M_n$ 1.33.

Example 43

Preparation of polystyrene macro-RAFT agent (1-PS) with methyl 2-(methyl(pyridin-4-yl)carbamothioylthio)propanoate (1) at 90° C.

A solution comprising 1,1'azobis(cyclohexanecarbonitrile) (VAZO-88) (12.2 mg), methyl 2-(methyl(pyridin-4-yl) carbamothioylthio)propanoate (1) (94.5 mg), p-toluenesulfonic acid (60.2 mg) and styrene (5 mL) was transferred to an ampoule which was degassed by three freeze-evacuate-thaw cycles, sealed and then heated at 90° C. for 2 h. To avoid unwanted cationic polymerization of styrene it is important, in making up the polymerization reaction mixture, that the p-toluenesulfonic acid is not added directly to styrene monomer. The ampoule was cooled, opened and the polymerization mixture was evaporated to dryness in vacuo. To ensure no trace of styrene monomer remained the polymer were then taken up in chlorobenzene and evaporated in vacuo several times until no styrene signals were detectable by $^1$H NMR. The characterization of the polystyrene prepared had $M_n$ 1850, $M_w/M_n$ 1.22.

Example 44

Preparation of Polystyrene-Block-Poly(Vinyl Acetate)

The following procedure is typical. A solution of polystyrene macro RAFT agent ($M_n$ 1850, 0.030 g, 0.01 M, from example 44), AIBN (1.4 mg, 0.005 M) and vinyl acetate (1.4 g) was transferred to an ampoule which was degassed by three freeze-evacuate-thaw cycles and sealed. The ampoule was heated at 70° C. for the times indicated in Table 18. The volatiles were removed in vacuo to give polystyrene-block-poly(vinyl acetate). Results are presented in Table 18.

TABLE 18

Molecular weight and conversion data for polystyrene-block poly(vinyl acetate) prepared at 70° C.

| Expt. | [Initiator]/ $10^{-2}$ M | $M_n/10^{3\,a}$ | $M_w/M_a$ | Time/h | Conv./% |
|---|---|---|---|---|---|
| 2 | 0.57 | 5.4(7.9) | 2.16(1.81) | 2.0 | 4.6 |
| 3 | 0.57 | 10.4(13.3) | 1.91(1.62) | 2.5 | 13 |
| 4 | 0.57 | 18.2(27.0) | 2.00(1.42) | 3.0 | 23 |
| 5 | 0.57 | 27.7(39.9) | 1.90(1.40) | 3.5 | 37 |
| 6 | 0.57 | 50.2(59.5) | 1.83(1.61) | 4.0 | 67 |
| 7 | 0.11 | 52.4 | 1.37 | 16.0 | 55 |

[a] Molecular weight and polydispersity data shown in parentheses were obtained using UV detector. set at 290 nm. This excludes contribution from dead polymer from the molecular weight distribution.

Example 45

Preparation of polystyrene-block-poly(methyl acrylate-grad-vinyl acetate)

The following procedure is typical. A solution of polystyrene macro RAFT agent ($M_n$ 1850, 13.5 mg, 0.01 M, from example 44), AIBN (0.12 mg, 0.005 M), vinyl acetate (605 mg) and methyl acrylate (32 mg) was transferred to an ampoule which was degassed by three freeze-evacuate-thaw cycles and sealed. The ampoule was heated at 70° C. for the times indicated in Table 9. The volatiles were removed in vacuo to give polystyrene-block-poly(methyl acrylate-grad-vinyl acetate). The resulting polymer is an example of one falling within the scope of formula (VIIa)

TABLE 19

Molecular weight and conversion data for polystyrene-block-poly(methyl acrylate-grad-vinyl acetate) prepared at 70° C.

| Expt | $M_n/10^3$ | $M_w/M_n$ | Time/h | Conv./% |
|---|---|---|---|---|
| 11 | 6.6 | 2.90 | 2.0 | 6.6 |
| 12 | 14.1 | 2.04 | 4.0 | 13 |
| 13 | 25.1 | 1.58 | 6.0 | 25 |
| 14 | 42.7 | 1.31 | 8.0 | 36 |

Example 46

Preparation of low polydispersity poly(N,N'-dimethyl acrylamide) using S-cyanomethyl N-methyl, N-(pyridin-4-yl)carbamodithioate (2) at 80° C.

A stock solution I of 2,2'-azobis[2-methyl-N-(2-hydroxyethyl)propionamide] (27 mg) in a volume of 5 mL ultrapure water was prepared in a volumetric flask. S-Cyanomethyl N-methyl, N-(pyridin-4-yl)carbamodithioate (2) (40.8 mg), p-toluenesulfonic acid monohydrate (35.4 mg), N,N'-dimethyl acrylamide (1.81 g), stock solution I (1 mL) and water (18.2 MΩ) to a volume of 10 mL was prepared in a volumetric flask. Aliquots (5 mL) of this stock solution were transferred to ampoules which were degassed by three repeated freezeevacuate-thaw cycles and sealed. The ampoules were heated at 80° C. for the times indicated in Table 20.

TABLE 20

Molecular weight and conversion data for poly(N,N'-dimethyl acrylamide) prepared with S-cyanomethyl N-methyl, N-(pyridin-4-yl)carbamodithioate (2) at 80° C.

| Entry | time/hr | $M_n$ | $M_w/M_n$ | % Conv. |
|---|---|---|---|---|
| 1 | 0.5 | 9,170 | 1.13 | 73 |
| 2 | 11 | 11,500 | 1.11 | 95 |

Example 47

Preparation of low polydispersity poly(N,N'-dimethyl acrylamide) using methyl 2-(methyl(pyridin-4-yl)carbamothioylthio) propanoate (1) in water at 80° C.

A stock solution I of 2,2'-azobis[2-methyl-N-(2-hydroxyethyl)propionamide] (27 mg) in a volume of 5 mL water (18.2 MΩ) was prepared in a volumetric flask. Stock solution II of methyl 2-(methyl(pyridin-4-yl)carbamothioylthio) propanoate (1) (24.7 mg), p-toluenesulfonic acid monohydrate (17.7 mg) in a volume of 5 mL water (18.2 MΩ) was prepared in a volumetric flask. Stock solution I (1 mL), stock solution II (5 mL) and water (18.2 MΩ) to a volume of 10 mL was prepared in a volumetric flask. Aliquots (2.5 mL) of this stock solution were transferred to ampoules which were degassed by three repeated freeze-evacuate-thaw cycles and sealed. The ampoules were heated at 80° C. for the times indicated in the Table 21.

TABLE 21

Molecular weight and conversion data for poly(N,N'-dimethyl acrylamide) prepared with S-cyanomethyl N-methyl, N-(pyridin-3-yl)carbamodithioate (9) at 80° C.

| Entry | time/hr | $M_n$ | $M_w/M_n$ | % Conv. |
|---|---|---|---|---|
| 1 | 2 | 24,900 | 1.16 | 84 |
| 2 | 4 | 25700 | 1.15 | >99 |
| 3 | 17 | 25160 | 1.16 | >99 |

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Many modifications will be apparent to those skilled in the art without departing from the scope of the present invention.

The invention claimed is:

1. A RAFT agent of formula (XI),

(XI)

where X is $NR^1$, $R^1$ is independently selected from optionally substituted alkyl, optionally substituted alkenyl, optionally substituted alkynyl, optionally substituted aryl, optionally substituted heteroaryl, optionally substituted carbocyclyl, optionally substituted heterocyclyl, optionally substituted arylalkyl, optionally substituted heteroarylalkyl, optionally substituted alkylaryl, optionally substituted alkylheteroaryl, and an optionally substituted polymer chain;

R* is a m-valent radical leaving group that affords R*, which initiates free radical polymerisation of one or more ethylenically unsaturated monomers;

m is an integer ≥1;

R* is selected from the group consisting of primary, secondary and tertiary cyanoalkyls, primary, secondary and tertiary alkoxycarbonylalkyls, and primary, secondary and tertiary carboxyalkyls; and where $Y^a$ is a Lewis base moiety selected from optionally substituted heteroaryl.

2. The RAFT agent of claim 1, wherein R* is selected from cyanomethyl, 1-cyanoethyl, 2-cyanopropan-2-yl, ethoxycarbonylmethyl, 1-ethoxycarbonylethyl, 2-cyanobutan-2-yl, 1-cyanocyclohexyl, 2-cyano-4-methylpentan-2-yl, 2-cyano-4-methoxy-4-methylpentan-2-yl, 2-cyano-4-carboxybutan-2-yl, 2-cyano-5-hydroxypentan-2-yl, cyano(phenyl)methyl, 2-alkoxycarbonylpropan-2-yl, 1-(butylamino)-2-methyl-1-oxopropan-2-yl, phenyl(ethoxycarbonyl)methyl, 1-(cyclohexylamino)-2-methyl-1-oxopropan-2-yl, 1-(2-hydroxyethylamino)-2-methyl-1-oxopropan-2-yl, and 1-(1,3-dihydroxy-2-(hydroxymethyl)propan-2-ylamino)-2-methyl-1-oxopropan-2-yl, 2-(4,5-dihydro-1H-imidazol-2-yl)propan-2-yl, and 2-(1-(2-hydroxyethyl)-4,5-dihydro-1H-imidazol-2-yl)propan-2-yl.

3. The RAFT agent of claim 1 selected from:

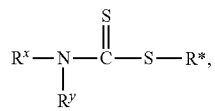

where $R^x$ is selected from an optionally substituted alky group or $R^y$; and $R^y$ is an optionally substituted pyridyl group (all isomers).

4. The RAFT agent of claim 3, wherein R* is selected from primary, secondary or tertiary cyanoalkyl.

* * * * *